US011532899B2

(12) United States Patent
Lazzi et al.

(10) Patent No.: US 11,532,899 B2
(45) Date of Patent: *Dec. 20, 2022

(54) FLUIDIC WIRE CONNECTORS

(71) Applicant: Teveri LLC, Salt Lake City, UT (US)

(72) Inventors: Gianluca Lazzi, Salt Lake City, UT (US); Dulce Maria Altabella Lazzi, Salt Lake City, UT (US); Kyle Loizos, Salt Lake City, UT (US)

(73) Assignee: Teveri, LLC, Salt Lake City, UT (US)

(*) Notice: Subject to any disclaimer, the term of this patent is extended or adjusted under 35 U.S.C. 154(b) by 0 days.

This patent is subject to a terminal disclaimer.

(21) Appl. No.: 17/181,952

(22) Filed: Feb. 22, 2021

(65) Prior Publication Data
US 2022/0037806 A1   Feb. 3, 2022

Related U.S. Application Data

(63) Continuation of application No. 16/773,743, filed on Jan. 27, 2020, now Pat. No. 10,931,036, which is a
(Continued)

(51) Int. Cl.
*H01R 3/08* (2006.01)
*A61B 5/024* (2006.01)
(Continued)

(52) U.S. Cl.
CPC ........... *H01R 3/08* (2013.01); *A61B 5/02444* (2013.01); *A61B 5/6804* (2013.01); *H01L 23/42* (2013.01);
(Continued)

(58) Field of Classification Search
CPC ............. A61B 5/6804; A61B 5/0816; A61B 2562/168; A61B 2562/166; A61B 5/02444; H01R 3/08; H01L 23/42
See application file for complete search history.

(56) References Cited

U.S. PATENT DOCUMENTS

| 4,166,666 A | * | 9/1979 | Reese | ...................... H01R 3/08 |
| | | | | 174/94 R |
| 5,626,484 A | | 5/1997 | Okuyama et al. | |
| | | (Continued) | | |

FOREIGN PATENT DOCUMENTS

| CN | 204885451 U | 12/2015 |
| JP | 2015133277 A | 7/2015 |

OTHER PUBLICATIONS

International Preliminary Report on Patentability for Application No. PCT/US2017/043407, dated Jan. 31, 2019 (8 pages).
(Continued)

*Primary Examiner* — Edwin A. Leon
(74) *Attorney, Agent, or Firm* — Alliance IP, LLC

(57) ABSTRACT

A connector to connect to a liquid metal wire includes a hollow conduit configured to connect to a tubular wire casing, and further includes a reservoir including a solid metal conductor. The reservoir is to receive liquid metal to substantially fill a volume of the reservoir such that the liquid metal extends into the tubular wire casing. The tubular wire casing, filled with the liquid metal, becomes the liquid metal wire.

20 Claims, 31 Drawing Sheets

Related U.S. Application Data continuation of application No. 16/319,336, filed as application No. PCT/US2017/043407 on Jul. 21, 2017, now Pat. No. 10,547,123.

(60) Provisional application No. 62/482,625, filed on Apr. 6, 2017, provisional application No. 62/365,171, filed on Jul. 21, 2016.

(51) Int. Cl.
    *A61B 5/00*      (2006.01)
    *H01L 23/42*      (2006.01)
    *A61B 5/08*      (2006.01)

(52) U.S. Cl.
    CPC ....... *A61B 5/0816* (2013.01); *A61B 2562/166* (2013.01); *A61B 2562/168* (2013.01)

(56) References Cited

U.S. PATENT DOCUMENTS

| | | |
|---|---|---|
| 5,993,269 A | 11/1999 | Ito |
| 7,147,478 B1 | 12/2006 | Ju |
| 7,731,513 B1 | 6/2010 | Lin |
| 10,411,380 B1 * | 9/2019 | Therien .............. H01R 13/5216 |
| 10,547,123 B2 * | 1/2020 | Lazzi ....................... H01R 3/08 |
| 10,931,036 B2 * | 2/2021 | Lazzi ................. A61B 5/02444 |
| 2010/0193243 A1 | 8/2010 | Hotte et al. |
| 2010/0238636 A1 | 9/2010 | Mascaro et al. |

OTHER PUBLICATIONS

PCT International Search Report and Written Opinion in PCT Application Serial No. PCT/US2017/043407 dated Sep. 29, 2017 (11 pages).

* cited by examiner

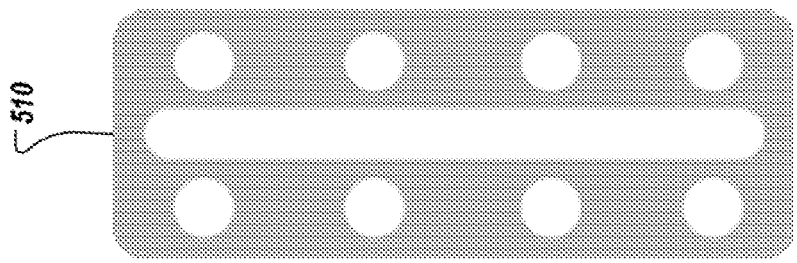
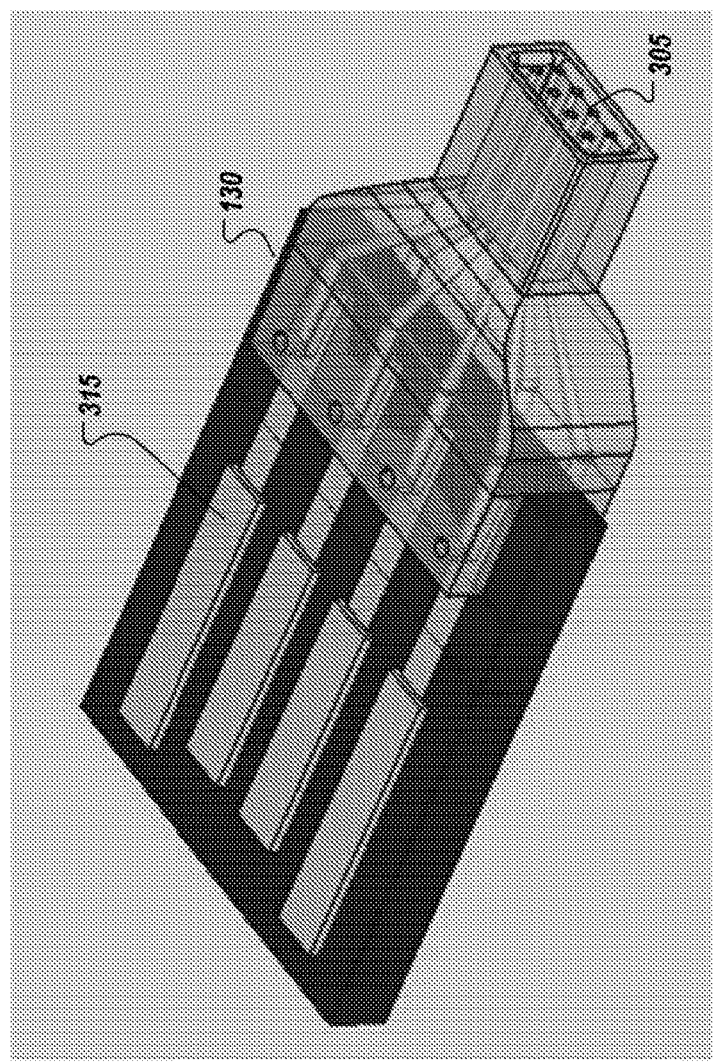
FIG. 6

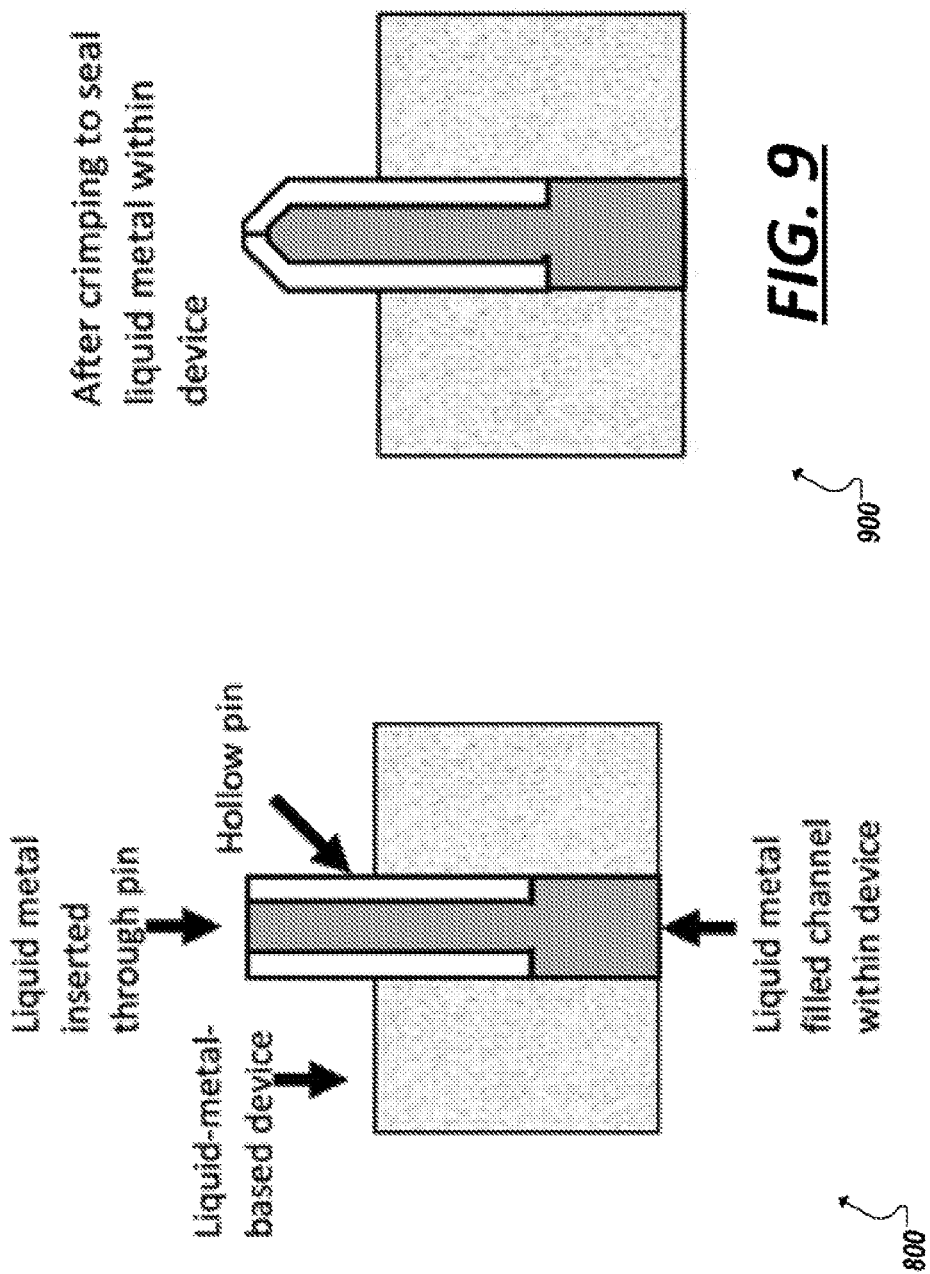

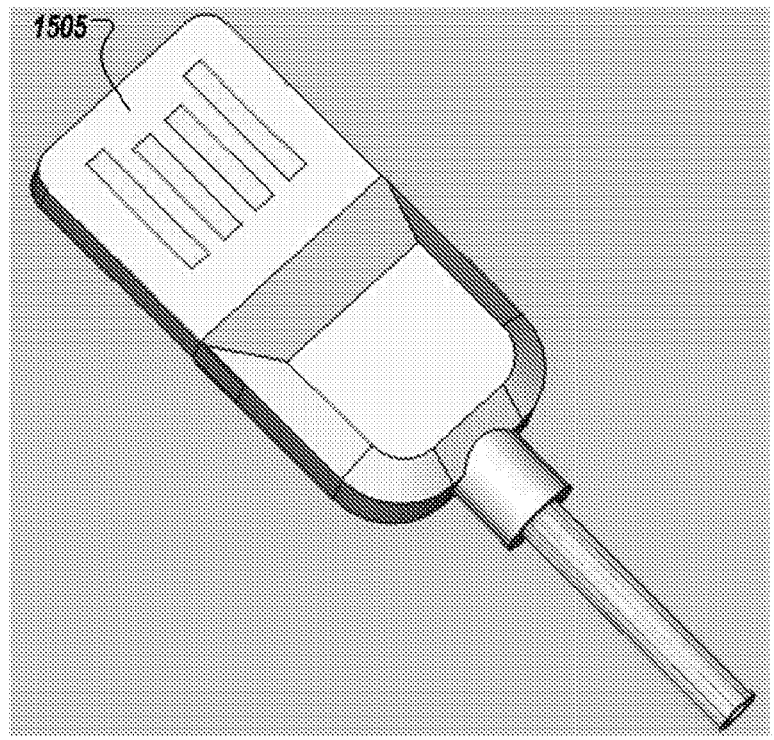
FIG. 15
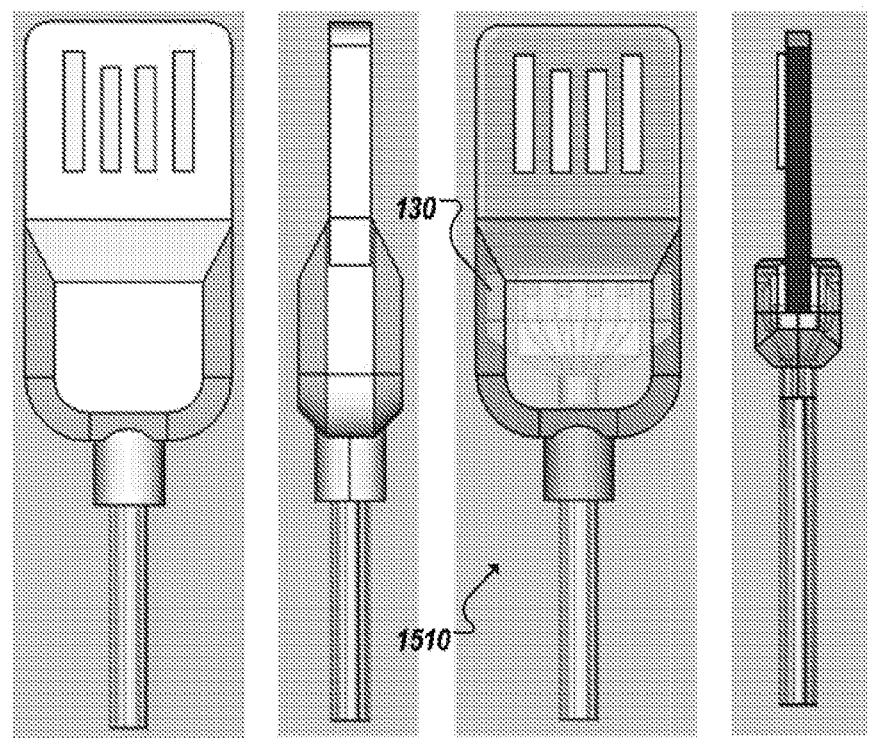

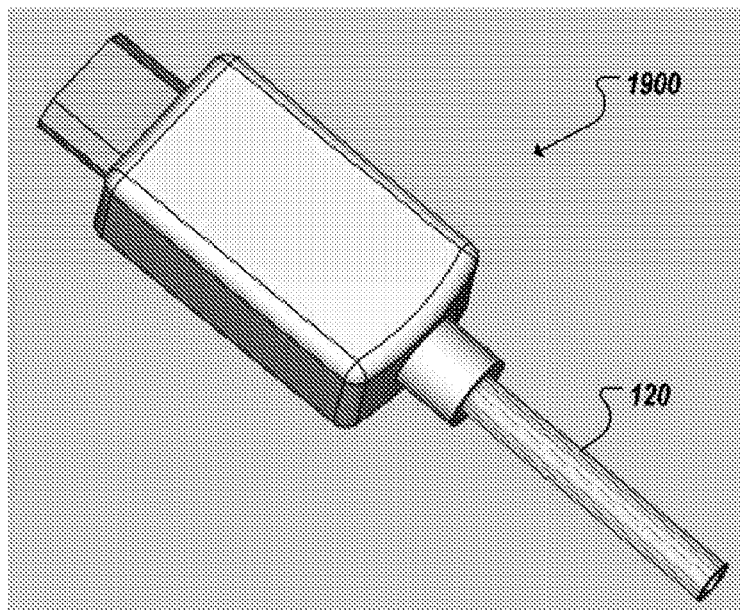
FIG. 19
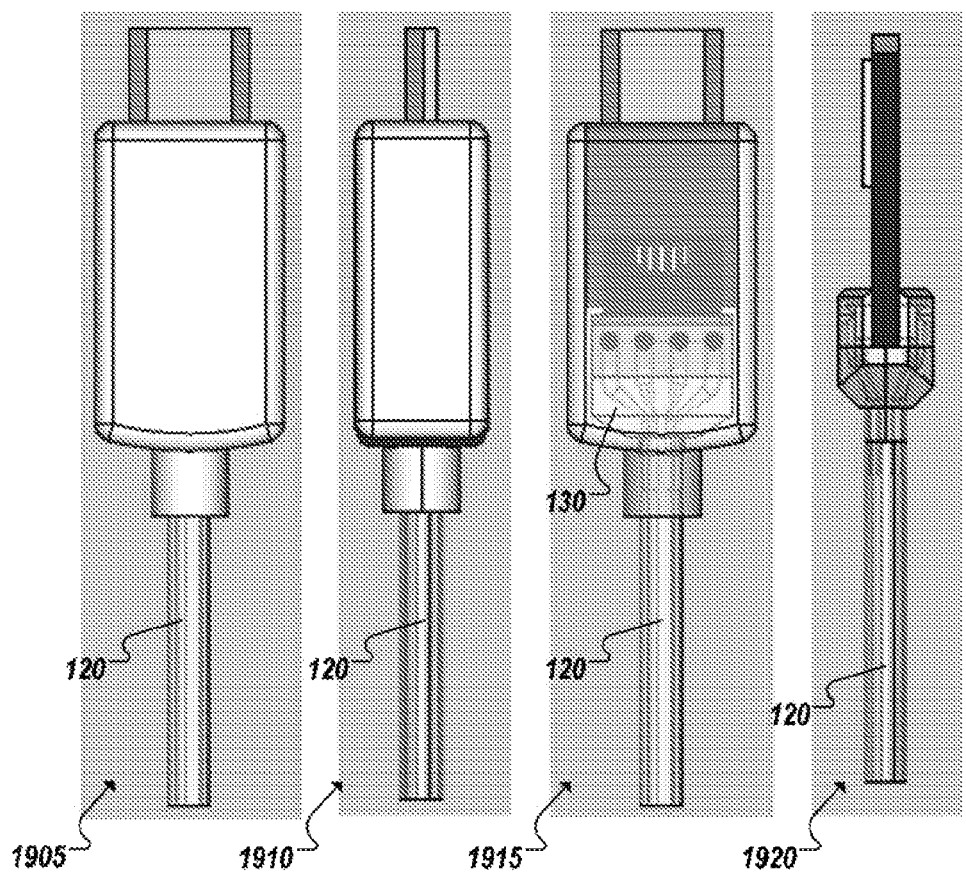

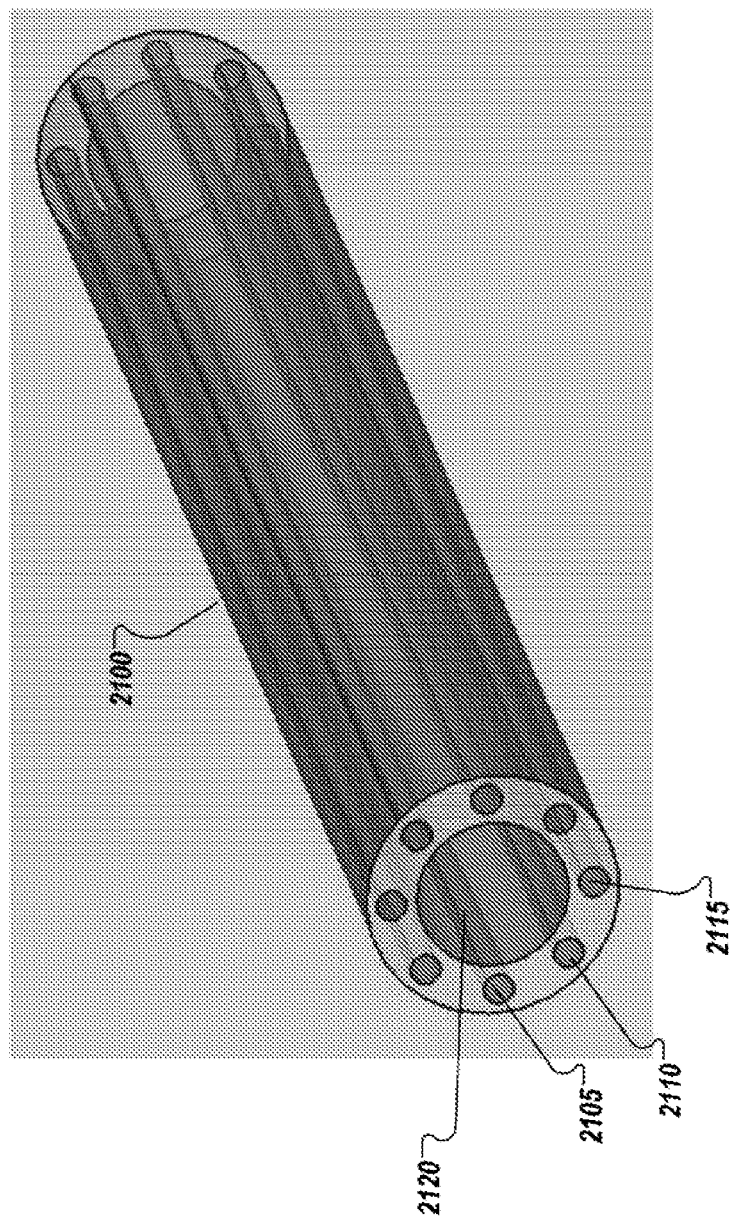

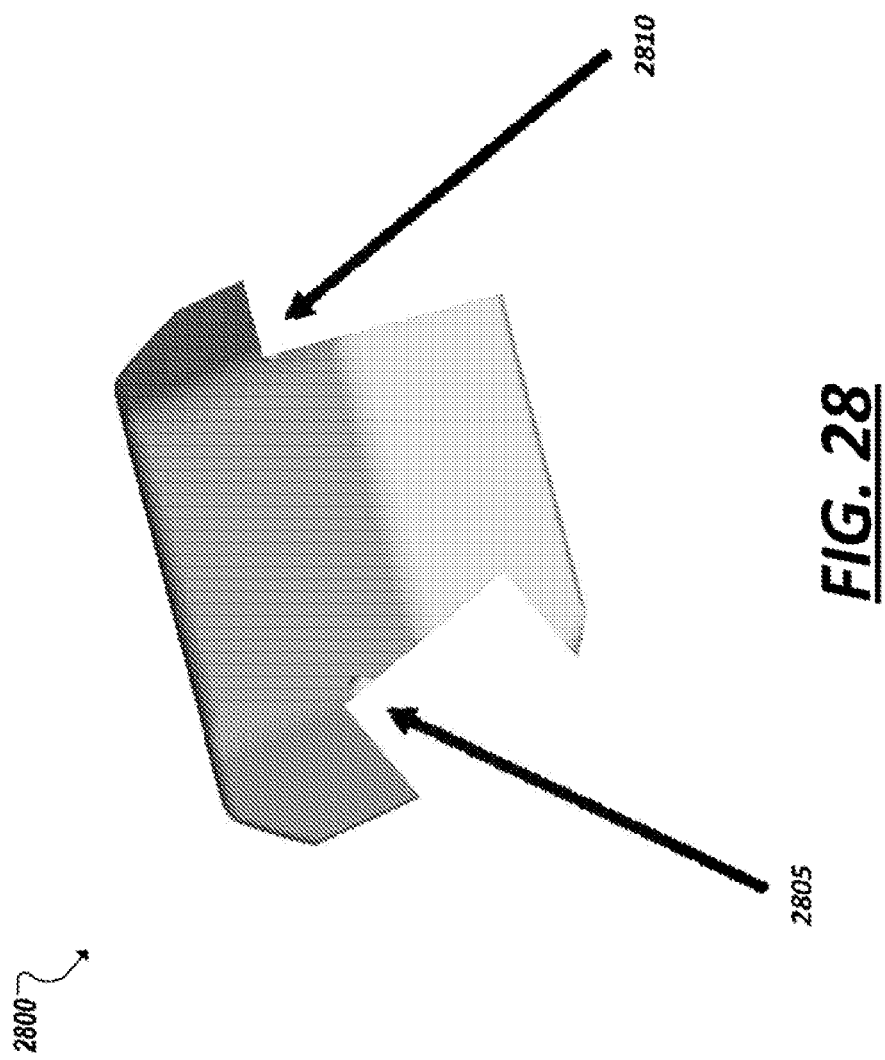

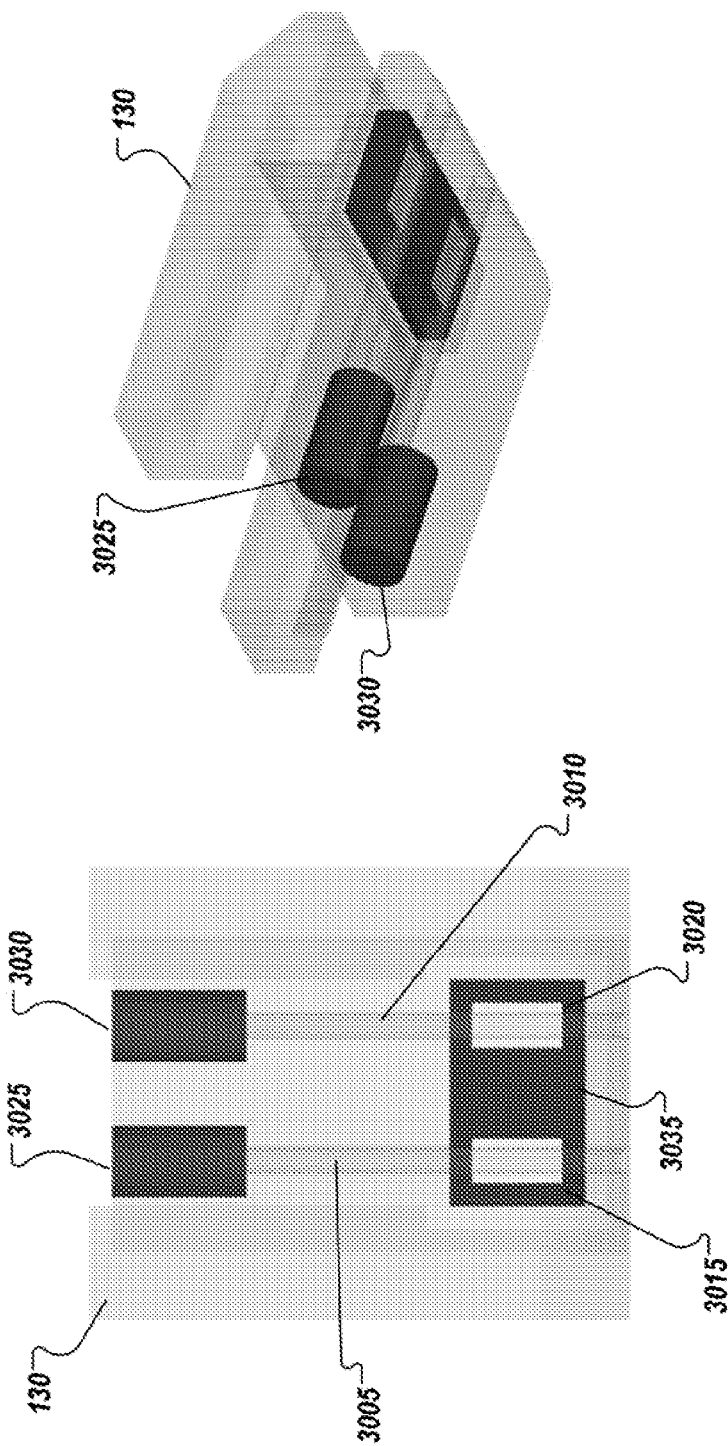

FLUIDIC WIRE CONNECTORS

This Application is a continuation (and claims the benefit of priority under 35 U.S.C. § 120) of U.S. patent application Ser. No. 16/773,743, filed on Jan. 27, 2020 and entitled FLUIDIC WIRE CONNECTORS, which application is a continuation of U.S. application Ser. No. 16/319,336, filed on Jan. 19, 2019, issued as U.S. Pat. No. 10,547,123 on Jan. 28, 2020, which application is a national stage application under 35 U.S.C. § 371 of PCT International Application Serial No. PCT/US2017/043407, filed on Jul. 21, 2017 and entitled FLUIDIC WIRE CONNECTORS, which application claims benefit of priority to U.S. Provisional Patent Application Ser. No. 62/365,171, filed Jul. 21, 2016, entitled LIQUID METAL INTERFACE and U.S. Provisional Patent Application Ser. No. 62/482,625, filed Apr. 6, 2017, entitled FLUIDIC WIRE CONNECTORS. The disclosures of the prior applications are each incorporated by reference herein in their entirety.

BACKGROUND

The present disclosure relates in general to the field of computer systems, and more specifically, to deformable electronic devices.

Computing devices such as personal computers, laptop computers, tablet computers, cellular phones, and countless types of Internet-capable devices are increasingly prevalent in numerous aspects of modern life. Over time, the manner in which these devices are providing information to users is becoming more intelligent, more efficient, more intuitive, and/or less obtrusive. The trend toward miniaturization of computing hardware, peripherals, as well as of sensors, detectors, and image and audio processors, among other technologies, has helped open up a field sometimes referred to as "wearable computing." A variety of wearable computing devices are being developed allowing electronic components to be carried on human and animal users.

BRIEF DESCRIPTION OF THE DRAWINGS

FIG. 6 illustrates a simplified schematic diagram of another example connector element.

FIGS. 8-9 illustrate simplified schematic diagrams of a portion of an example connector element.

FIGS. 15-20 illustrate simplified schematic diagrams of views of another example connector element.

FIG. 21 illustrates simplified schematic diagram of an example fluidic wire casing to implement multiple liquid metal wires.

FIG. 28 illustrates simplified schematic diagrams of a portion of an example connector element.

FIGS. 30A-30B illustrate views of an example connector element including caps made from self-healing material.

Like reference numbers and designations in the various drawings indicate like elements.

DETAILED DESCRIPTION

Figure 1:
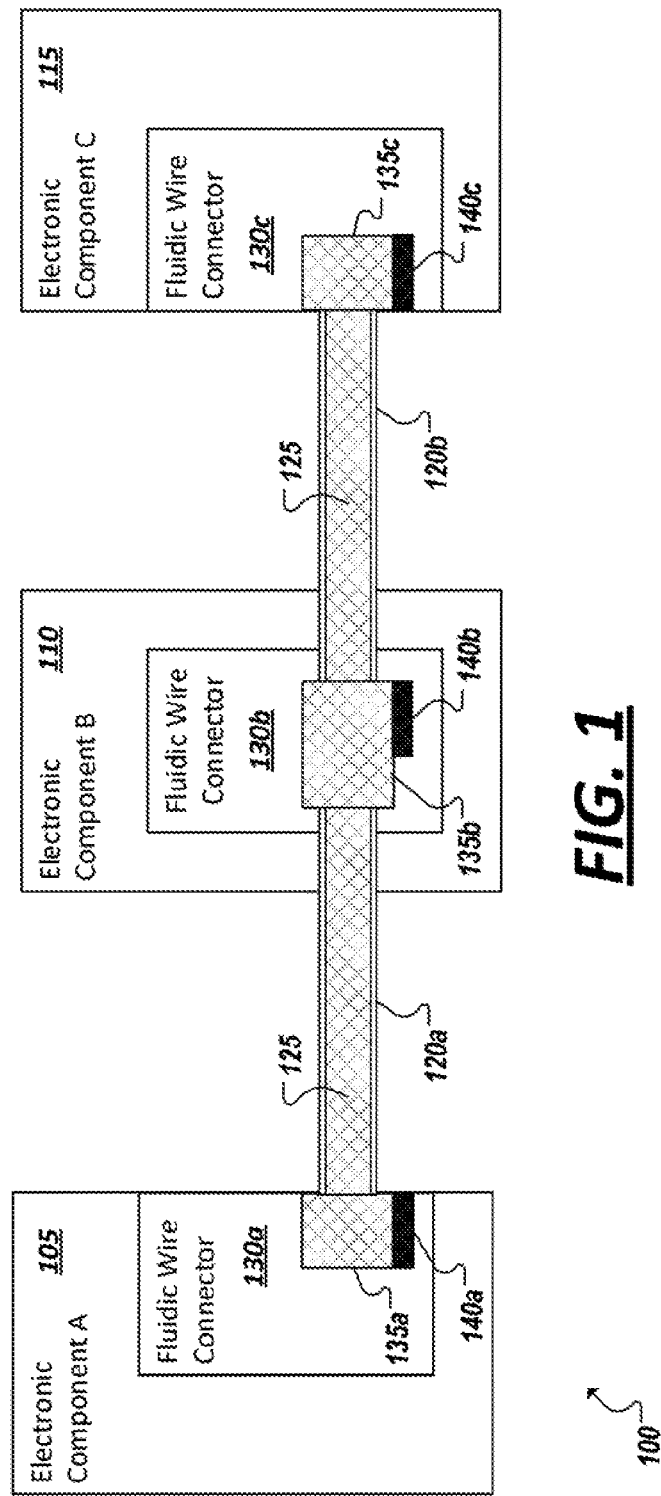
FIG. 1 illustrates a simplified schematic diagram of an example system connecting electronic components with one or more liquid metal wires.

The subject matter described herein provides for components to connect to reversibly deformable and mechanically tunable fluidic wires (also referred to herein as "fluidic cables" or simply "cables"). The reversibly deformable and mechanically tunable fluidic wires may be formed by injecting a liquid metal, such as gallium or a gallium-based alloy, into one or more sheaths or other cavities within a material substrate or a base material (e.g., coupled to a bonding layer material). Any conductive liquid metal that has a melting point below an ambient liquid metal wire manufacturing facility temperature or the temperature of the desired operating environment may be used such that heating of the liquid metal is not required for the liquid metal to be introduced during manufacturing or for the liquid metal to retain its deformable properties in application. An example temperature range from negative twenty degrees Celsius (−20° C.) to forty degrees Celsius (40° C.) may be used in association with certain of the metals described herein that are in a liquid state within this range, though it is understood that other temperature ranges may be appropriate for other implementations of liquid metal to be used to form a reversibly deformable and mechanically tunable fluidic wire. In one example, eutectic gallium indium (EGaIn) has a melting point of fifteen and seven tenths degrees Celsius (15.7° C.) and given the supercooling property of gallium may maintain this liquid property at temperatures even lower than its melting point, allowing EGaIn (and other gallium-based alloys) to be used as the liquid metal within an example fluidic wire. As such, a lower end of the ambient liquid metal wire manufacturing facility temperature range for such an implementation may be considered, for example, sixteen degrees Celsius (16° C.). Other metals and temperature ranges may be used for formation of liquid metal wires that may have higher or lower melting points, and as such, different ambient liquid metal wire manufacturing facility temperature ranges.

In some cases, a fluidic wire may be constructed by injecting the liquid metal into a wire housing or sheath, or other cavity. As an alternative to injecting a liquid metal into one or more cavities, the liquid metal may be drawn into a cavity by applying a vacuum or other pulling force to the liquid metal via the cavity. In either implementation, injecting or drawing the liquid metal into the cavity may be terminated in response to the cavity filling to capacity. Alternatively, filling the cavity may be terminated on demand by cessation of the filling process upon filling of the cavity to an extent sufficient to allow radiation of electromagnetic energy via the fluidic wire. Inlet and outlet filling hole locations may be provided for the respective operations, and the cavity may be sealed in response to filling the cavity.

The term "fluidic wire" and "liquid metal wire" may be used interchangeably to represent a wire with a liquid metal resonant element. The term "material" and "substrate" may be used interchangeably to represent a substance within which a fluidic wire may be formed. The term "cavity" may be used to represent a hollow channel, capillary, conduit, sheath, groove, furrow or other structure within a substrate within which liquid metal may be filled to form a fluidic wire. The terms "cavity," "channel," "artery," and "capillary" or other terms may be used interchangeably hereafter to identify a void or other structure, within one or more portions of material that define a shape of a fluidic wire within the material, that may be filled with liquid metal to form a fluidic wire. For certain implementations, a channel may be considered a "microfluidic channel."

The material within which the cavity and fluidic wire are formed may include a flexible and/or stretchable material, for example, an elastomer such as silicone or other polymer-based materials. Other examples of flexible materials include polymer films, composite substrates, gels, thin metal supports, and other flexible materials. The material within which the cavity and fluidic wire are formed may also include rigid materials such as wood, dry wall, polymeric parts, polymer films, gels, and other rigid materials. It is understood that the present subject matter applies to any material that may form a cavity that may define a shape of a fluidic wire without interfering with spectral properties of the fluidic wire beyond interference acceptable within a given implementation, and all such materials are within the scope of the present subject matter.

A cavity may be formed into a substrate in a variety of manners. Because the wire is formed with a liquid metal, the mechanical properties of the wire may be defined by mechanical properties of the substrate. As such, for an elastomeric substrate, the resulting elastomeric fluidic wire may be deformed (e.g., stretched, bent, flexed, rolled, etc.) and released/reversed without loss of electrical continuity. As a consequence, the resulting wires may be more durable relative to conventional technologies and may be utilized in applications that would otherwise result in destruction of conventional wires. Strain may be induced in a material, for example, in response to temperature changes, pressure changes, mechanical load changes, geographical changes, or any other change that results in a force on the material that deforms, elongates, shrinks, or otherwise changes the material's dimensions. For example, the fluid metal may flow in response to strain (e.g., elongation) of the elastomeric substrate, resulting in a reconfiguration of the geometry of the fluidic wire and a resulting shift in the resonant frequency of the wire, while returning to its original geometry and frequency response upon removal of the applied strain. Based upon these properties, the fluidic wire is considered to have no or minimal hysteresis, as defined by the mechanical properties of the substrate in response to mechanical strain and release of mechanical strain.

Fluidic wires may be coupled to electronic components to provide power to or enable signaling between components in an electronic system. In some cases, connectors element or other interfaces may be utilized to facilitate an electric coupling between a component and a fluidic wire. While traditional wires utilize solid metal to implement connectors, such constructions may present a variety of challenges in fluidic wire-based solution. For instance, a connection may be made between a solid metal contact and a liquid metal wire by inserting a solid metal pin into the end of a liquid metal cable with a small diameter opening (e.g., 1-3 mm). In such an instance, the contact point is the endpoint of the metal pin, resulting in a small surface area in contact with the liquid metal and, as a result, a relatively weak electrical connection. Further, when filling liquid metal cables with liquid metal, it may be desirable to ensure an optimum volume and/or pressure within the wire casing. However, inserting a solid metal pin into a filled (or partially filled (in anticipation of the introduction of a solid metal connector)) liquid metal wire, may jeopardize achieving the optimum volume and pressure characteristics of the wire, among other example issues. In some implementations, the diameter of the pin can be designed such that it behaves as a check valve, allowing liquid metal to only flow into the cable, ensuring a defined volume of liquid metal will remain within the cable.

To address at least some of the issues above, a device, or connector, may be provided to serve as an interface between the liquid metal of a liquid metal wire and an electrical connector used to couple the wire to another wire or an electronic component. In such implementations, the connectors may be provided with hollow channels to allow liquid metal to flow freely from the wire into the channel and into contact with electrical pads, hollowed pins, or other metal surfaces facilitating an electrical connection.

For instance, in the simplified block diagram 100 of FIG. 1, an example system is shown including electronic components (e.g., 105, 110, 115), such as sensors, user interfaces, power sources, processors, memory, buttons, light emitting diodes (LED), among other examples. The components may be interconnected using liquid metal wires (e.g., 120*a-b*). FIG. 1 illustrates a cross-sectional view of the wires and connectors (e.g., 130*a-c*) used to couple the wires 125*a-b* to the components 105, 110, 115. As illustrated in this example, the liquid metal wires may be filed with liquid metal 125 (represented in this illustration by shaded areas of FIG. 1). Each of the components 105, 110, 115 may be provided with a respective connector element (e.g., 130*a-c*), either added to or integrated with the components 105, 110, 115, which enables solid metal conductors to interface with the liquid metal of the liquid metal wires 120*a-b* and complete an electrical connection between components (e.g., between components 105 and 110 and components 110 and 115) using the liquid metal wires 120*a-b*.

In the particular example of FIG. 1, each connector 130*a-c* may include a channel and reservoir (collectively represented in FIG. 1 by 135*a-c*), whereby a fluidic wire (e.g., 120*a-b*) may be inserted into the connector, or alternatively, whereby the connector may be inserted into the fluidic wire and allow liquid metal of the wire to pass freely into and at least partially fill the reservoir 135*a-c* of the connector. Each connector 130*a-c* may additionally include a solid metal conductor 140*a-c* at least partially exposed within the reservoir 135*a-c* of the connector that is to come into contact with the liquid metal to form an electrical connection with the liquid metal (e.g., 125) in the fluidic wire 120*a-b*. It should be appreciated that the system of FIG. 1 is provided as an example only, as a variety of different systems may be implemented, which incorporate fluidic wires to interconnect various components of various types. While such systems may include connector elements (e.g., 130*a-c*) that utilize reservoirs to bring liquid metal into contact with solid metal, a combination of different connectors and connector types may be utilized in some implementations without deviating from the scope of the present disclosure.

Figure 2:
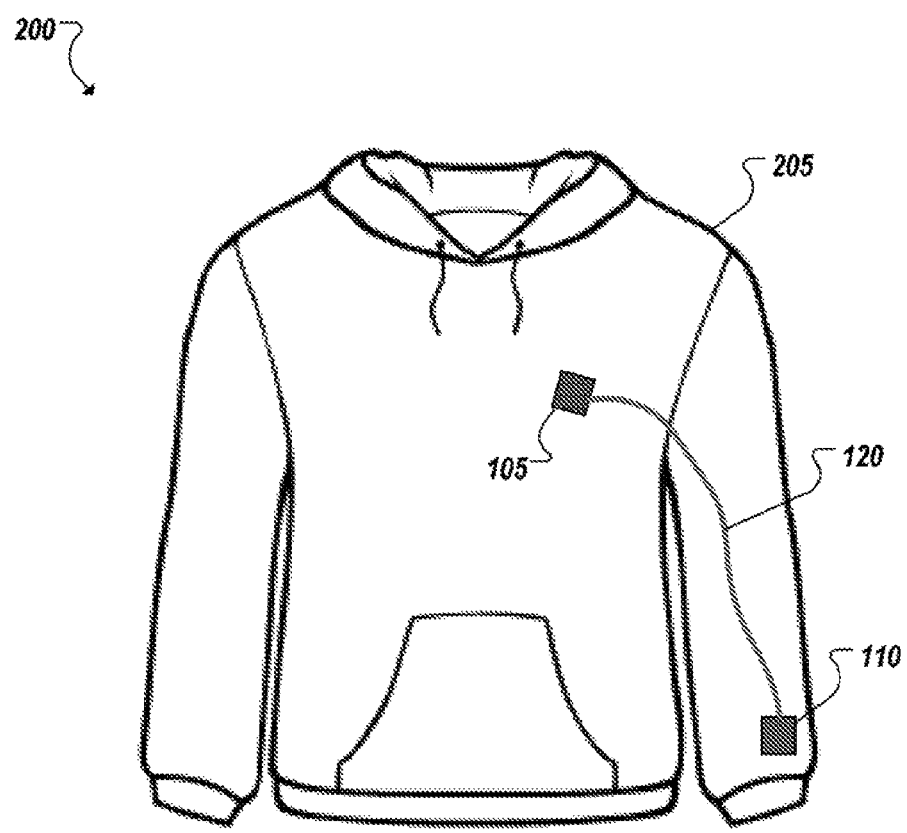
FIG. 2 illustrates a simplified block diagram of an example wearable device including a liquid metal wire.

The elastic and flexible nature of fluidic wires may allow the fluidic wires to be integrated into a variety of applications where solid metal wires may be suboptimal. For instance, some devices may be integrated in, come in regular contact with, or be carried or worn in such a way that the device (and the wires interconnecting the components of the device) is regularly compressed, folded, bent, twisted, bounced, etc. As but one example of such an article, wearable devices may be provided, which are to be worn or carried by a human, animal, robot, etc. Such wearable devices may utilize fluidic wires to carry power and/or signals within the device (and even out from the device to peripheral devices or components which may be attached to the wearable device). For instance, as shown in the simplified illustration 200 of FIG. 2, a wearable garment 205 is provided to which one or more electronic components (e.g., 105, 110) have been attached (e.g., adhered, interwoven, sewn, clipped, or otherwise attached). A fluidic wire 120 may be utilized to connect the two components 105, 110. For instance, a heart rate monitor (e.g., 105) integrated into the garment 205 may be connected to a display (e.g., 110) by a fluidic wire made of one or more lumens (e.g., adapted to carry the signaling between the two components 105, 110). In some examples, the fluidic wire may be integrated, adhered, interwoven, or otherwise connected to the fabric of the garment 205 itself. A variety of other articles may be composed of components utilizing fluidic wires as antennae or as connective links to other components.

Figure 3:
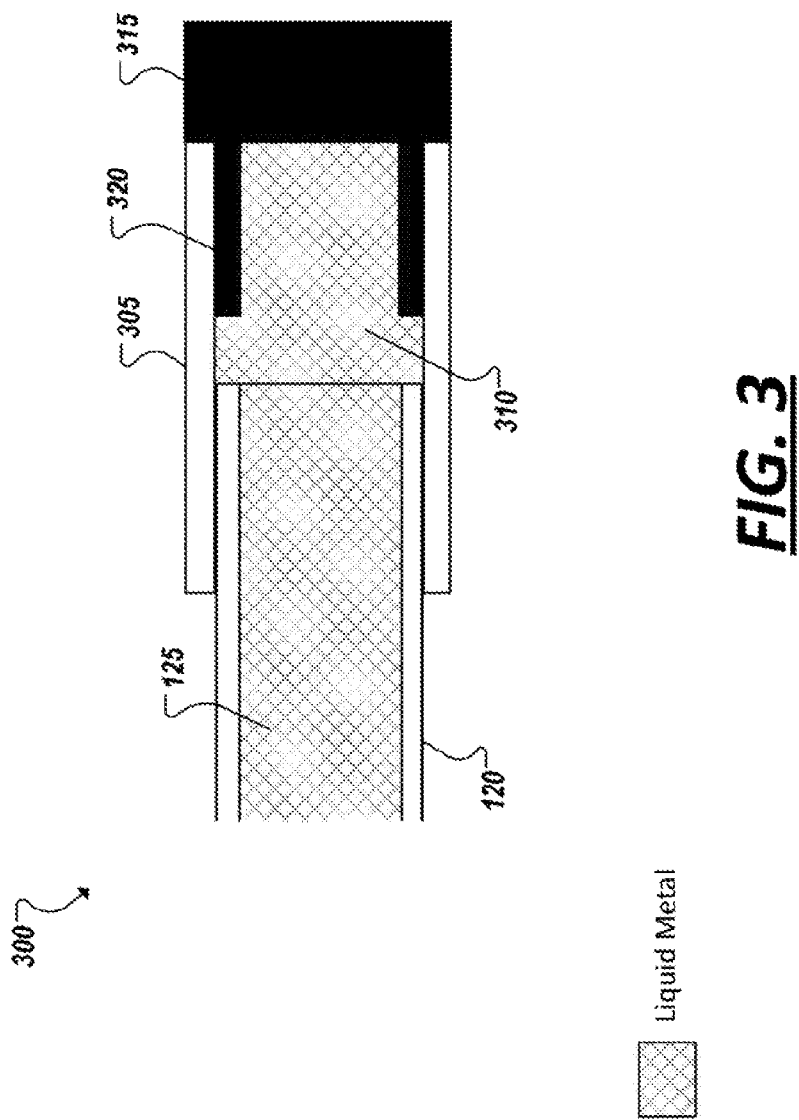
FIG. 3 illustrates a simplified block diagram representing connection of a connector element to a liquid metal wire.

Turning to FIG. 3, a simplified block diagram 300 is shown of an example conduit 305, which may at least partially extend from a connector and provide a path for liquid metal to extend from a liquid metal wire 120 to a reservoir of a connector that further includes a conductive solid metal surface (e.g., 320). In this particular example, the conduit 305 may be dimensioned such that a fluidic wire casing with a particular outer diameter may be passed within the inner diameter conduit, to establish a channel from the interior of the fluidic wire into the conduit and a reservoir of a connector. In other examples (such as the example shown in FIG. 7), the interior dimensions of a connector conduit (or "hollow pin") may allow for the conduit to pass within the inner diameter of the fluidic wire casing. While the use of the term diameter may suggest substantially round dimensions of wire casings and connector conduits, it should be appreciated that potentially any geometry may be utilized (e.g., with conduit and wires having rectangular, triangular, or other shapes), with the corresponding dimensions being adapted to allow for a fluidic wire casing to pass inside the channel of a connector conduit, or for a connector conduit to pass inside a fluidic wire casing. The dimensions of a wire casing and conduit may be adapted to allow one to fit snugly within the other. However, in order to prevent leakage of liquid metal between the fluidic wire and the connector the connection of the fluidic wire with the connector may be sealed so as to not allow leakage.

In one example, such as shown in FIG. 3, a fluidic wire and connector conduit may be mated to connect the connector to the fluidic wire casing prior to the introduction of liquid metal into the system. For instance, upon connecting a wire to a connector, the wire and connector may form a unified channel in which liquid metal may be injected (e.g., to flow from the wire into the reservoir or to flow from the reservoir into the wire), among other examples. With the liquid metal (e.g., 125) introduced into the wire 120 and connector reservoir 310, the liquid metal may be brought into contact with solid metal connectors (e.g., 320), which may extend further to provide current through further solid metal- or semiconductor-based circuitry (e.g., 315).

Figure 4:
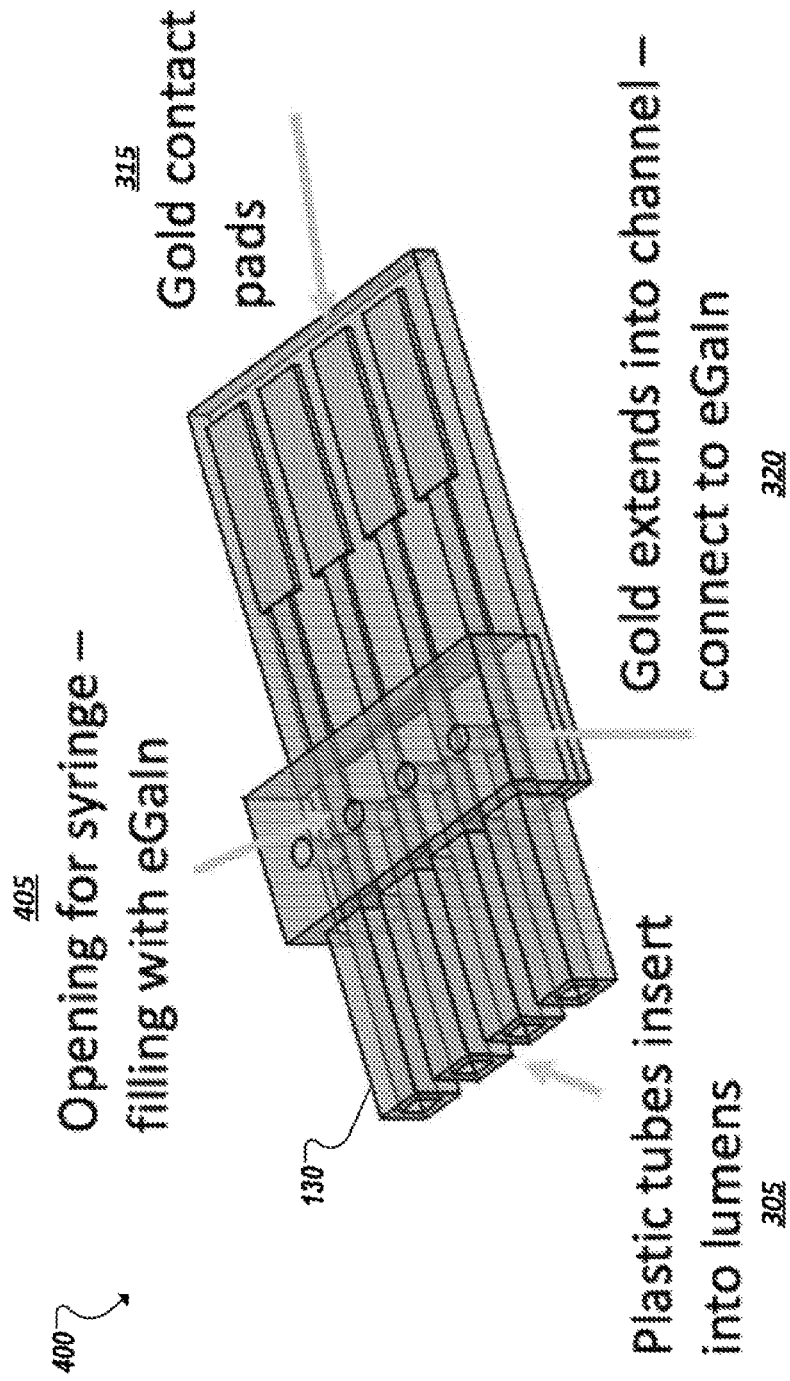
FIG. 4 illustrates a simplified schematic diagram of an example connector element.
Figure 5:
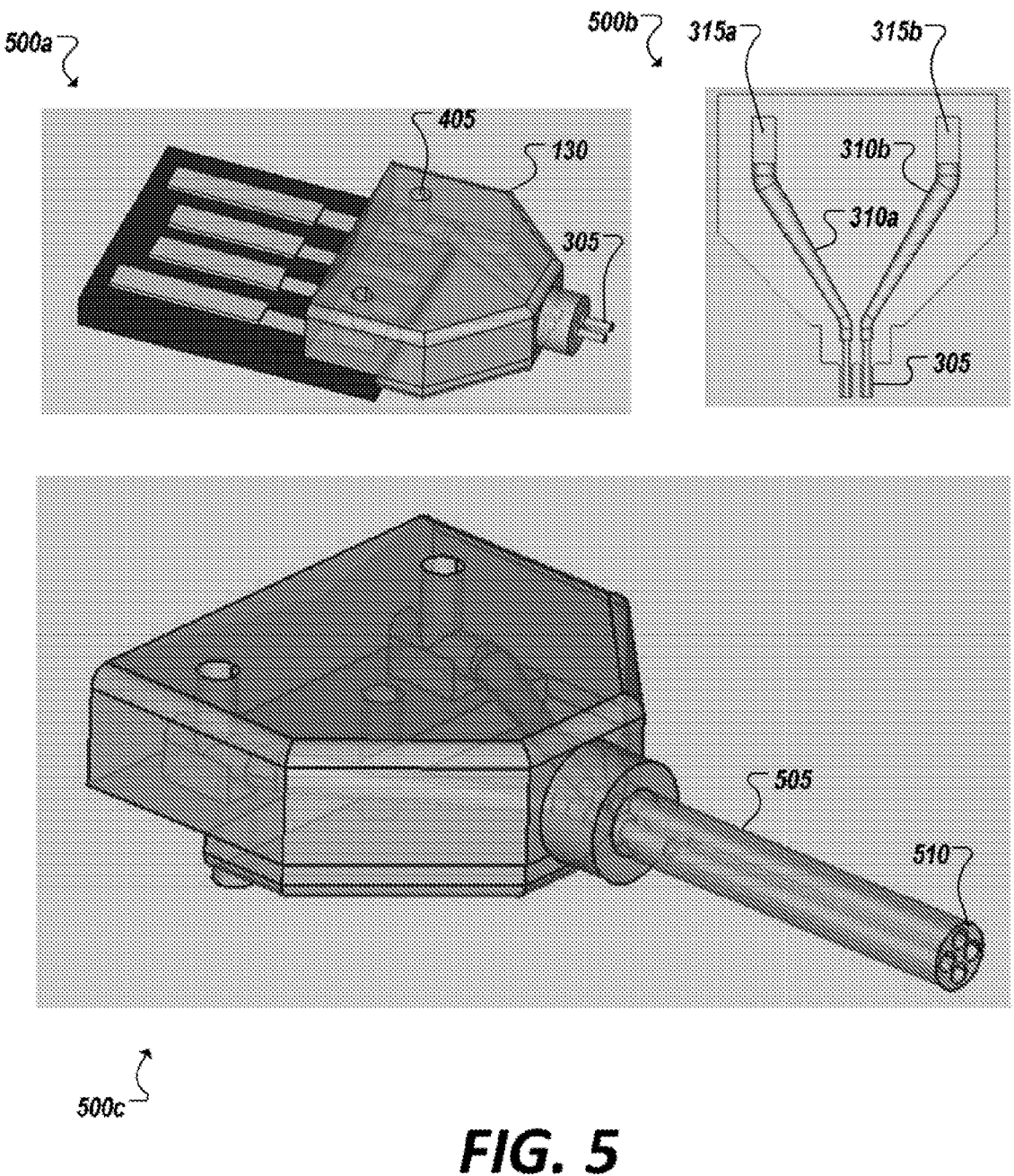
FIG. 5 illustrates a simplified schematic diagram of another example connector element.

As noted above, to attach to liquid metal devices, hollow tubes (or conduits) may protrude from the surface of the device (or a connector attached to the device). Hollow conduits may refer to any set (single or multiple) of solid or flexible polymer, metal, or other material that are hollow and organized appropriately for fitting into multi-lumen tubing, a single or set of individual tubes, or other devices housing liquid metal, such as terminals for a flexible antenna. Such conduits 305 may have any cross-sectional geometry depending on the specific application (e.g., square as shown in the example of FIG. 4, round as shown in the example of FIGS. 5 and 6, etc.). In some cases, multiple conduits, or tubes, may be provided on a connector to enable multiple different fluidic wires to be connected (e.g., to support signaling over multi-wire connections). The individual tubes may be kept a distance apart from each other to separate the individual liquid metal conductors and allow for them to be inserted into the device reservoirs housing the liquid metal. In some implementations, a surface with openings may be used without having these hollow tubes protruding, allowing for the liquid-metal-housing devices to be sealed against the surface, having the openings in these devices (e.g., tubing, flexible electronics, etc.) line up with the openings on an interfacing or connector device, and sealed using adhesive, UV welding, thermal fusion, solvent bonding, or any other example mechanism for sealing around each opening. This may also allow for devices that have needles or individual tubes to be inserted into this interfacing device or connector. In addition, a sleeve, flexible polymer, or other sealing mechanism may be provided around this connection point between a fluidic wire and the conduit of a liquid metal connector of a device in order to add structural integrity, to limit flexibility or add rigidity, and so forth.

Continuing with the above examples, the openings to a reservoir-based connector provided through these conduit tubes form channels within an interfacing device. These channels can have any geometry, extending the geometry of the liquid metal device it is connecting to (such as illustrated in the example of FIG. 4), or modifying the geometry throughout the channel to match the solid electrical connector it is interfacing with (such as illustrated in the examples of FIGS. 5-6). An opening to the channel allows for filling the channel, and liquid metal device it is attached to, with liquid metal. This opening may then be sealed with adhesive or by bonding a second piece of material that can either match the geometry of the opening or be placed against the surface. This bonding can be accomplished using adhesive, UV welding, thermal fusion, solvent bonding, or any other form of sealing to ensure that liquid metal does not leak out of the device. Additionally, this opening may be kept sufficiently small such that liquid metal is not able to exit, but large enough that a needle can be used to fill the device, serving as an inherent valve.

In some examples, channels may be either constructed of, or lined with (partially or fully) a conductive medium, such as, but not limited to, gold or nickel plating. This conductive contact may extend out of the device, allowing it to be connected to a solid electrical connector. This conductive surface can either be incorporated into the channel, or be part of an external surface, such as a printed circuit board (PCB) each (such as in the examples of FIGS. 5-6). For instance, the channels may have an opening with the walls around this opening being sealed against liquid metal leaking. An opening in the channel allows for the channel to be exposed to the conductive surface rather than lining the channel itself.

In some implementations, a connector adapted to connect devices to fluidic wires may be implemented in an electronic device and serve to fill, seal and cap the liquid metal introduced to the devices. Solid metal leads in contact with the liquid metal may then extend to connect to other circuits in the device. In some implementations, the device may be a connector or cable (e.g., according to a particular connector specification), to allow connections to other devices, such as through a Universal Serial Bus (USB), audio, Lightning, High Definition Multimedia Interface (HDMI), or other connection. For instance, as shown in the example of FIG. 4, a device 130 is shown that includes four rectangular conduits (e.g., 305) which may be inserted into corresponding lumens, or wire coverings, to enable a connection between the device 130 and corresponding fluidic wires. The hollow channels 320 provided through the conduits 305 allow liquid metal to enter the connector device 130 and touch the metal surfaces of conductors that embody or connect to sold metal contact pads 315 which may be used to connect to the other device. In this example, openings 405 are additionally provided on a connector element 130 to allow liquid metal to be piped into the channels 320 and flow into the empty wire coverings connected on the conduits (305) to fill the coverings and form fluidic wires connected to the connector element 130. In some implementations, all or a portion of the connector (or at least the opening 405) may be constructed from a self-healing material (e.g., natural rubber, silicone, or other materials), such that a syringe or other deposition mechanism may be temporarily inserted into the openings 405 to inject liquid metal up to the desired volume and pressure and then remove the syringe while leaving the connected channel sealed against the escape of the newly injected liquid metal, among other example implementations.

FIGS. 5 and 6 show additional implementations of connector elements according to some alternative designs. For instance, in the example of FIG. 5, a connector 130 is shown (in view 500a) that includes two conduits 305 to feed liquid metal from wires connected to the conduits to reservoirs 310a,b in contact with two solid metal pads 315a,b (as shown in view 500b). View 500c illustrates the connection of a liquid metal wire casing 505 to be inserted over the conduits 305. In this example, rather than two separate wire casings, a single casing 505 may be provided that has multiple channels traversing the casing, which may each be filled with liquid metal (e.g., using injections sites 405 provided on the connector 130) to form a respective liquid metal wire. Such a multi-wire casing may have a cross-section with channel openings (e.g., 510) to mate with one or more different, compatible connector conduit orientations (e.g., 305). FIG. 6, shows a view 600 of another example of a connector element 130 similar to the example in FIG. 5, but with a different set and orientation of conduits (e.g., 305) adapted to connect to multiple fluidic wires in a system and allow liquid metal to complete a circuit by coming in contact with solid metal surfaces of contact 315. The resulting cross-section of conduits arranged in the example of FIG. 6 could connect to a multi-wire casing with an opening (and channels) corresponding to the example cross-section 510 shown in FIG. 6, among a variety of other potential examples.

An improved interfacing device for use with liquid metal devices may possess example advantages over traditional solutions. For instance, through the use of conductive hollow channels with external solid leads, external electronics may interface with liquid metal filled devices as if they were solid conductors. As another example, the use of channels within such an interfacing device allows for the reorganization of different leads from the liquid metal based device. This may be particularly useful for applications in which liquid metal is used in small tubing. The ability to change the channel geometry allows for it to be enlarged, simplifying post-processes for filling and sealing the device with liquid metal. As another example advantage, by using hollow channels and having the ability to inject the liquid metal after sealing a device to a solid external device, higher control over the filling of liquid metal may also achieved. When attempting to interface a liquid metal device with solid electronics using solid conductive pins, or other solid conductors that are inserted into the liquid metal, the pressure and/or volume of liquid metal inside a device can be difficult to control. By having a hollow, reservoir-based system, which includes an opening for filling without having to insert the electrical contact into the liquid metal device, parameters such as volume or pressure of the liquid metal can be controlled using external filling systems, such as pressure-controlled syringe pumps, without concern for inserting a conductor after filling. Further, the devices described herein may allow for application-specific devices to be designed, with inherent conductivity built into channels for interfacing between the two devices. Additionally, by using hollow channels, liquid metal may be injected into the devices after sealing to the external connectors or other electrical devices. This may avoid the risk of leaking liquid metal during processes for attaching external electronics, among other example advantages.

In some implementations, a conductive surface may be provided in reservoir-based connectors to line any amount of the inner surface of the conduit channels, which extends outside the channel, allowing it to be accessed by external processes to form electrical connections from an external device to the liquid metal inside. The channels have opening(s) for connecting to liquid-metal devices. This allows for conductive liquid metal to extend into these channels and form an electrical connection with the conductive surface within this device, and therefore make an electrical connection with an external solid electrical connector. An opening may be added to the channels for filling this interfacing device and the liquid metal based devices with liquid metal, allowing for increased control of the filling process, as opposed to filling the devices prior to attaching to external solid contacts.

Figure 7:
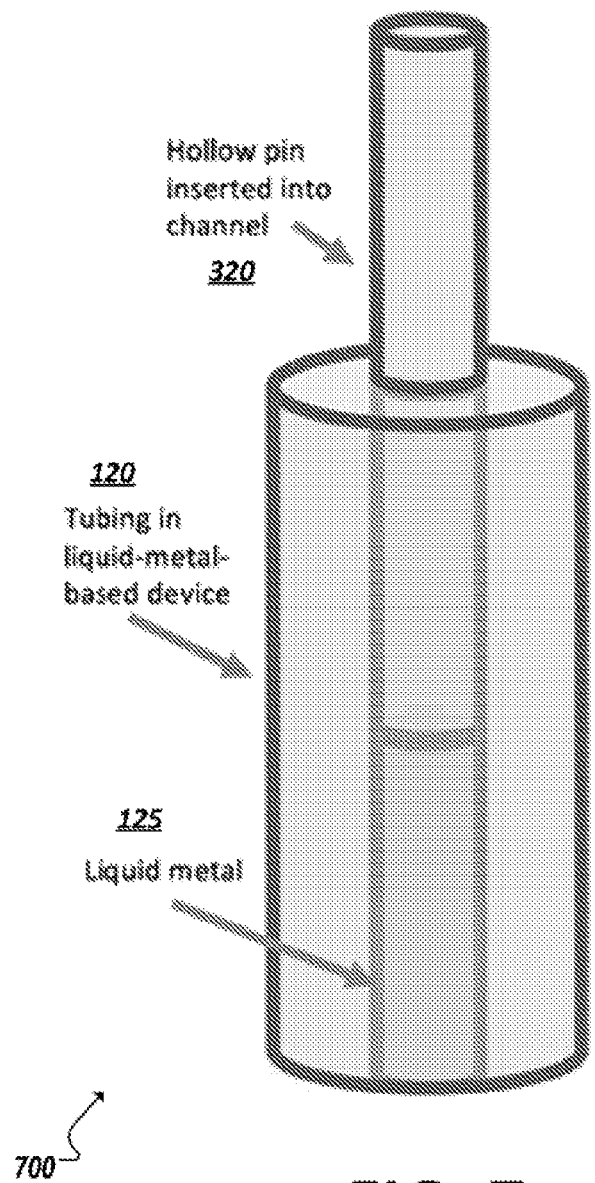
FIG. 7 illustrates a simplified schematic diagram of an example conduit of an example connector element.

In some implementations, such as illustrated in FIGS. 7-9, hollow metal pins may be used to implement conduits to interface liquid metal cables and electrical connectors. Such conduits, or pins, may have a hollow tubing of potentially any geometry (i.e. rectangular, circular, etc. depending on the application), either made of a conductive material or with conductive material on the surface (i.e. stainless steel or copper pins, or tubes made of a non-conductive material such as silicon or a thermoplastic with gold, platinum, etc. plated, sputtered, or otherwise bonded to the surface). The liquid metal can fill one or more lumens within a stretchable cable 120. The metal conduit pins 320 may be inserted into these terminals or lumens prior to filling with liquid metal 325, such as shown in the example of FIG. 7. In some implementations, a conduit inserted into an opening of a fluidic wire casing (such as shown in FIG. 7) may serve as a check valve, allowing for liquid metal to remain within the cable without being forced out, up to a pre-defined pressure that is decided by the inner diameter of the pin. Further, such pins may serve as an electrical contact, allowing current to pass from one pin, through the liquid metal and through the pin on the other side, interfacing with one or more electrical connectors. Such pins can further ensure electrical contact. By filling the cables with liquid metal through the hollow pins, the pins and cable are filled with liquid metal. This allows for contact of the pin with the liquid metal for the entire length of the pin, and maintains sufficient volume within the cable. Additionally, pins can be used to control filling processes. By attaching pins prior to filling and filling through the pins, not only is electrical contact ensured within the inner walls of the pins, but it allows for a clean filling process by not requiring the filling apparatus to be removed and a solid conductor to be inserted for electrical connection. Additionally, this allows some control over the pressure inside the pins and liquid-metal-based devices. During filling, when a desired pressure or volume is reached, the pins may be crimped or capped, such as shown in the examples of FIGS. 8 and 9, sealing the ends to avoid leaking and maintaining the desired pressure or volume within the device(s).

While at least some of the examples above illustrated the use of a reservoir-based connector element to connect and create a conductive coupling at an end of a fluidic wire and cap the opening of the fluidic wire, in other example implementations, a connector element may be provided at a point before the beginning or end of a fluidic wire at potentially any distance along a fluidic wire cable or tubing. For instance, rather than or in addition to allowing components to connect at the ends of a fluidic wire, connector elements may be positioned in-line with (i.e., between the ends of) a single wire. For instance, component elements can be attached to the fluidic wire, where the component provides one or more reservoirs and/or channels that are lined (partially or fully) with a solid conductive medium, similar to implementations shown and described above, to bring the solid conductor into contact with conductive liquid metal. The conductive surface of a connector element's reservoir can extend out of the channel, and also allow for connecting to other electrical components, such as lighting devices, heating elements, sensor elements, display elements, etc. These devices may be exposed to the liquid conductive medium directly, or via an intermediary component, such as a printed circuit board whose conductive pads serve as the interfacing conductive surface or lead to a connector that extends into the liquid conductor-filled channel. In some implementations, the intermediary component may itself be or incorporate a reservoir-based connector element that is configured to connect to a fluidic wire inline, among other examples.

Figure 10:
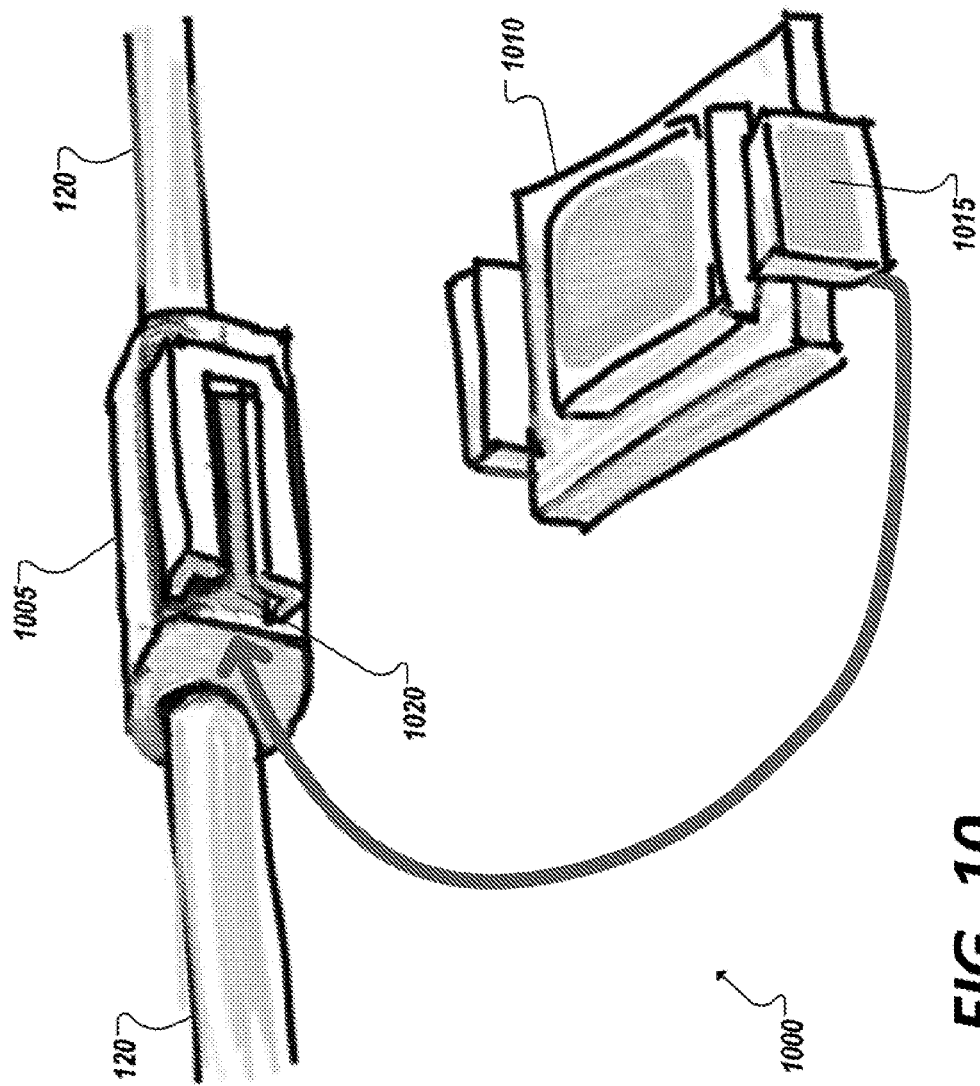
FIG. 10 illustrates a simplified schematic diagram of another example connector element to accept detachable components.

Turning to the diagram 1000 shown in the example of FIG. 10, in some implementations, a connector element 1005 may be provided to couple to a fluidic wire and bring liquid metal into contact with the connector conductive surfaces to enable the connector element to support removable components (e.g., 1010), which may be removably attached to the connector element to allow a conductive surface 1015 or interface of the component 1010 to be brought into contact with a conductive surface 1020 of the connector element 1005, which is at least partially in contact with liquid metal that extends into the liquid wire 120. This may allow removable components 1010 (e.g., interchangeable sensors, LEDs, etc.) to be attached and removed from the intermediary component/connector (e.g., 1005), which is attached (at the end of or in line with a fluidic wire). The connector component 1005 (such as illustrated in the example of FIG. 10) may include a solid conductive contact that interfaces with the liquid metal inside of the fluidic wire (e.g., as in other embodiments discussed herein), and a mechanism to physically attach removable or attachable components 1010 to the connector (e.g., through a magnet, clip, sliding mechanism, button, spring loaded pins, or other connector technology implemented on the connector element (e.g., 1005) and/or the removable component (e.g., 1010)). Additionally, this mechanism can ensure alignment of the components for maintaining electrical contact. In this way, implementations utilizing fluidic wires connected to such connector elements may allow the application (e.g., a smart garment or textile) to become modular, allowing users to customize the components that are added, moved, removed, and replaced using the connector element (e.g., 1005).

In implementations of a component capable of connecting directly to fluidic wire, the component housing may include reservoirs or channels with potentially any number of inlets and outlets, each corresponding to a particular fluidic wire to be attached to the component at a respective tube/channel and allowing for liquid metal from each of these wires to access the corresponding electrical contact within the component housing. So, in addition to capping the end of a cable, a connector element serving to interface liquid metal with terminal electrical components such as a power source, USB connector, audio connector, heating element, or lighting device, electrical components can be attached in-line without terminating the electrical continuity of the tubing, among other example implementations.

Figure 11:
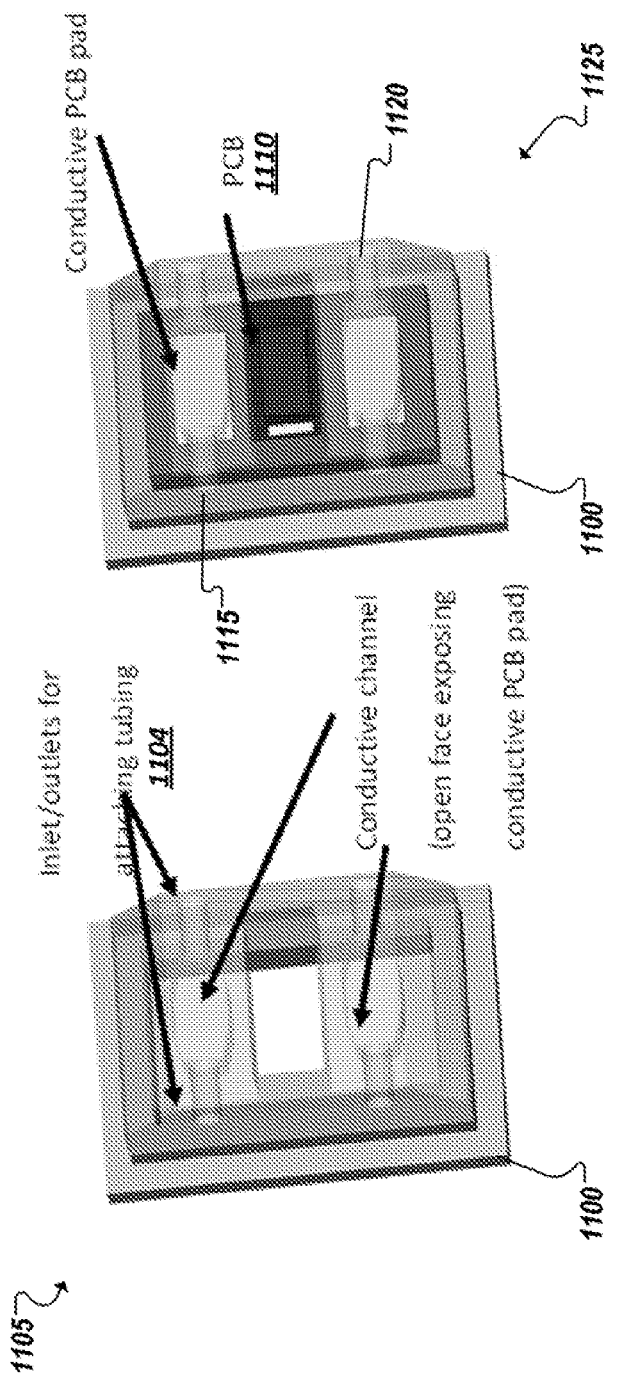
FIG. 11 illustrates a simplified schematic diagram of another example connector element.
Figure 12A:
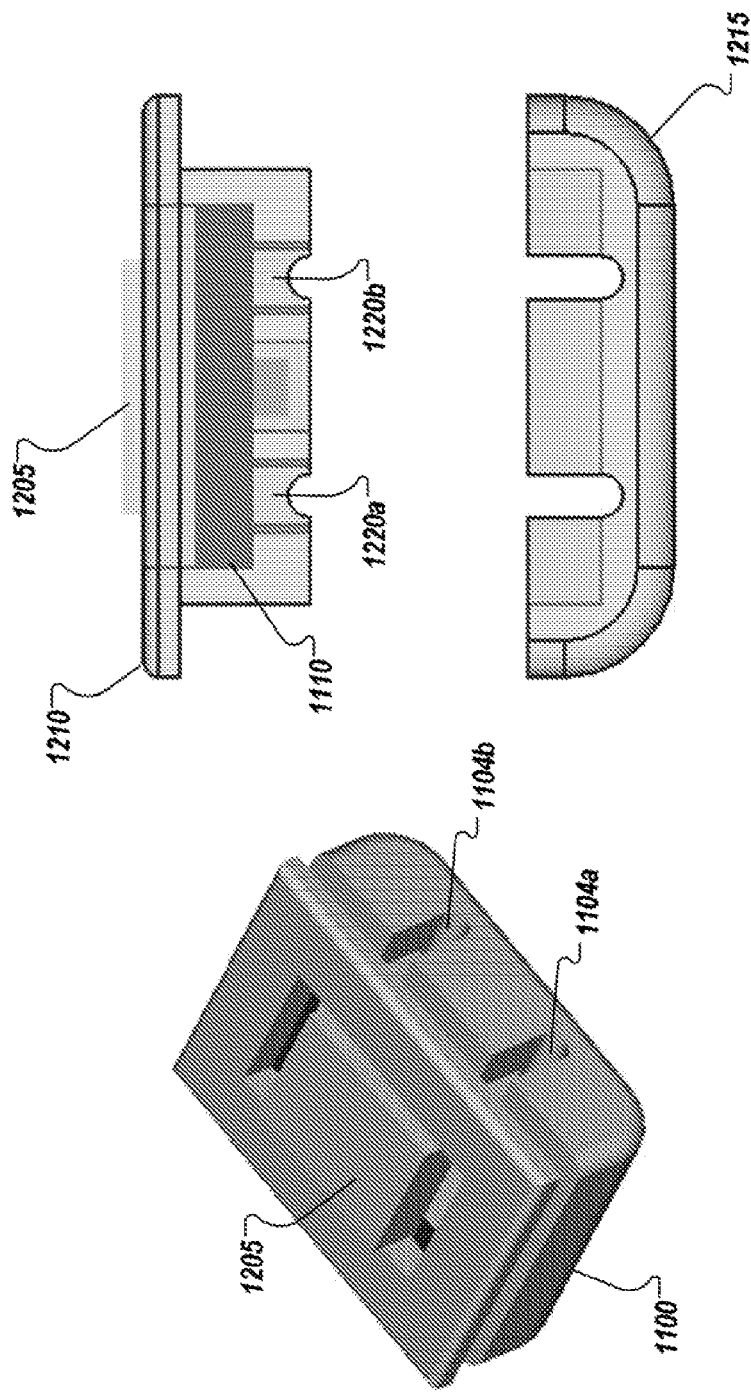
FIG. 12A illustrates a simplified schematic diagram of another example connector element.
Figure 12B:
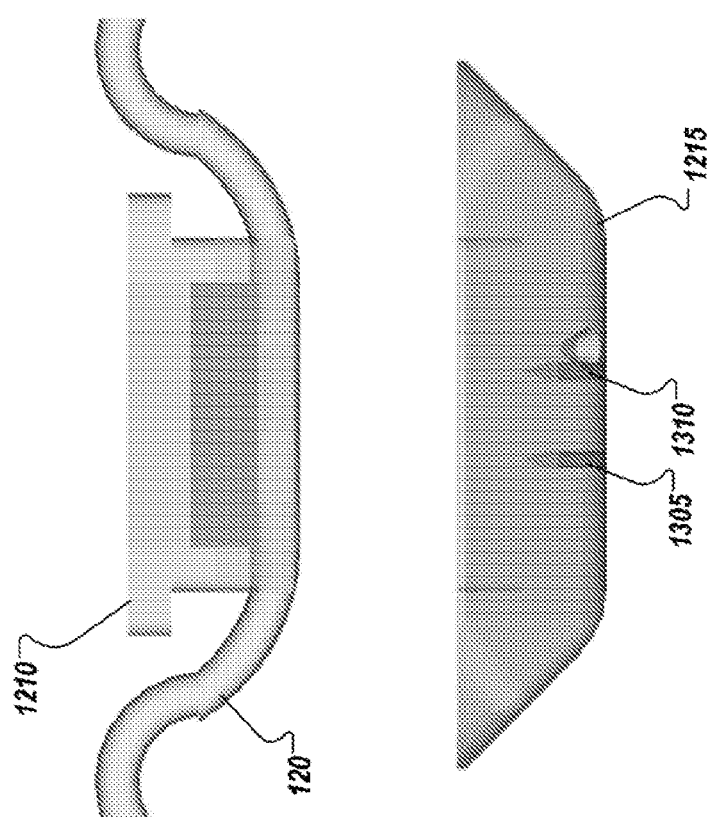
FIG. 12B illustrates a simplified schematic diagram of another example connector element.

In one example, an in-line attachment to a fluidic wire can be accomplished by severing the tubing or cable and attaching either end to the inlet(s) and/or outlet(s) of the housing, or the housing can itself be designed to sever the tubing upon attachment (through the use of micro needles for puncturing the surface of the tubing (e.g., as shown in FIG. 12B), severing the tubing via pinching it between two features of the housing, or otherwise forcibly puncturing the tubing and allowing liquid metal to exit the tubing and allow electrical contact to both the interface within this housing, as well as continuing to maintain electrical connectivity along the length of the tubing. This device can be a single part 1100, as shown in FIG. 11 below, or it can be composed from multiple parts, with an example shown in FIGS. 12A-12B. FIG. 11 shows an example housing for interfacing individual liquid-metal-filled tubes with a printed circuit board (PCB) or other electrical component. FIGS. 12A-12B shows two-piece designs for connector elements adapted to attaching in-line to a fluidic wire In the example of FIG. 11, as shown at 1105, the housing 1100 includes inlets and outlets 1104 through which fluidic wires may be attached to the housing 1100. A conductive channel or reservoir 1115, 1120 may be provided which may be filled with liquid metal which is to continue from a reservoir into the channels of the fluidic wires attached in-line to a pair of liquid metal filled tubes. As shown in view 1125, the placement of the reservoirs 1115, 1120 may correspond to the location of conductive pads of an electronic component that is to be connected in-line with the fluidic wire. For instance, in FIG. 11, a custom printed circuit board (PCB) 1110 is used to interface with the liquid metal via conductive pads placed strategically in order to line the channel 1115, 1120 in the housing 1100 and interface with the liquid metal introduced through the liquid metal filled tubes (or "fluidic wires"). These fluidic wires may be implemented as fibers, tubes, or cables independently, or integrated into fabric for use with wearable technologies, such as Lightning, heart rate or respiration sensors, audio interconnects, etc.

In the examples of FIGS. 12A-12B, an in-line connector element 1100 is shown that is composed of two or more pieces, which may be assembled around a fluidic wire. For instance, a first piece 1210 of the connector element 1100 may include an electronic component, such as the PCB 1110 of the example of FIG. 11. Additional components (e.g., 1205) may be mounted on the PCB 1110, such as an LED, processor, sensors, or other component. The first piece 1210 may additionally include cavities 1220a,b to correspond to the placement of reservoirs that are to form upon assembly of the connector element 1110 and correspond to the location of conductive pads of the PCB 1110. A second piece 1215 may be provided which is to connect with the first piece 1210 to form the connector element 1110. For instance, fluidic wires may be introduced to the inlet/outlet openings (e.g., 1104a,b). In one example, the fluidic wires may be already filled with liquid metal and may be slit, pierced, or pre-provided with openings such that the liquid metal leaks into and fills the cavities (e.g., 1220a,b) of the connector element 1100 when enclosed using second piece 1215, among other example implementations. In some instances, the act of enclosing a fluidic wire within the connector element 1100 by connecting pieces 1205, 1210 to form a reservoir within the connector may simultaneously act to prick, cut, or otherwise penetrate the outer surface(s) of the fluidic wire to allow liquid metal to leak into the reservoir and thereby establish a connection with the component (e.g., 1110).

For instance, as shown in the example of FIG. 12B, one of the pieces (e.g., 1215) of a multipiece connector element 1110 may be provided with sharp, pin elements (e.g., 1305, 1310), which, when brought into contact with a fluidic wire 120 (e.g., when the piece is positioned to connect to another one of the components), may puncture the fluidic wire and cause liquid metal to leak from the fluidic wire into the reservoirs created when the connector element pieces are assembled.

Figure 13:
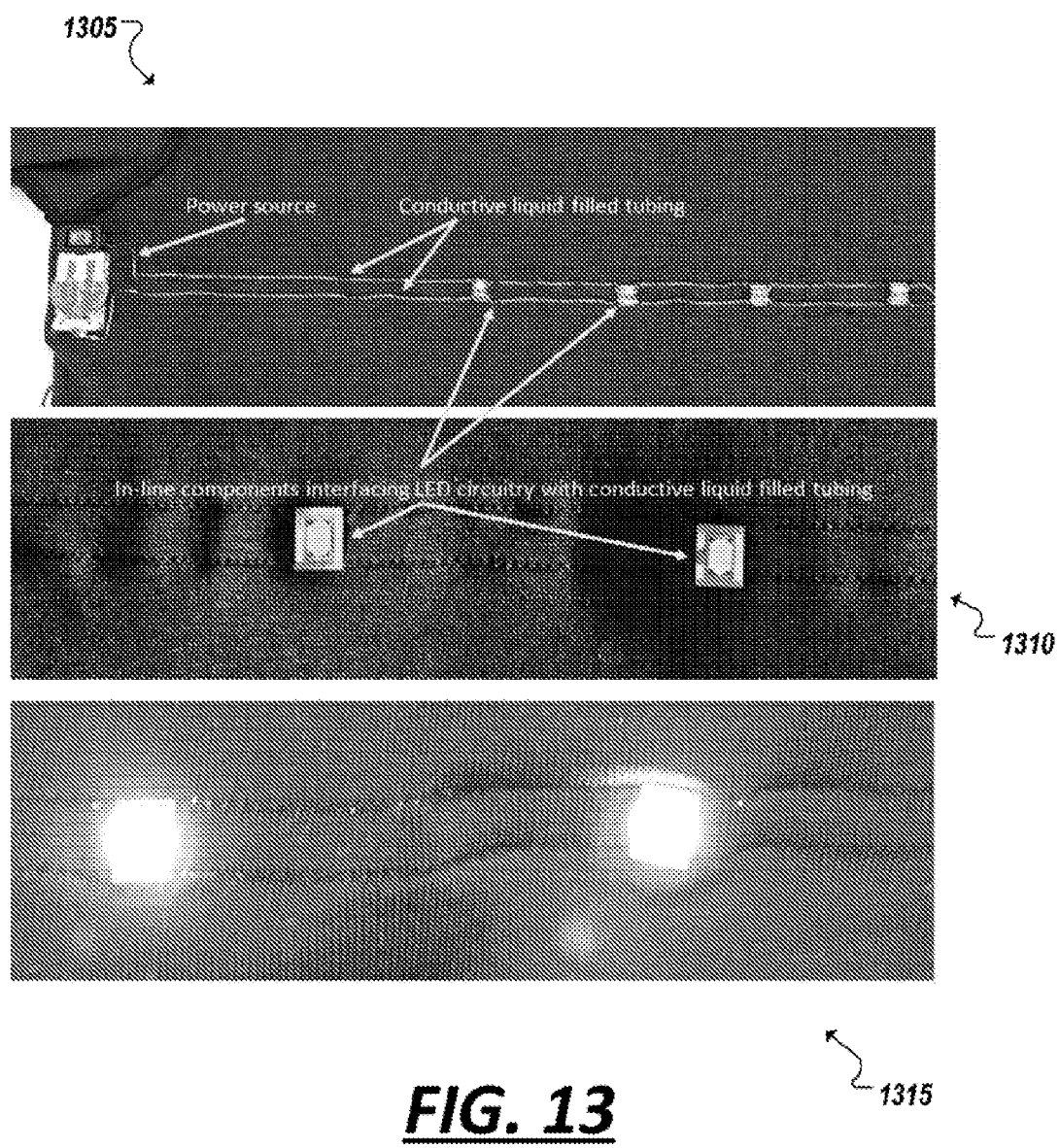
FIG. 13 are photographs showing components connected to a liquid metal wire fastened to fabric.
Figure 14:
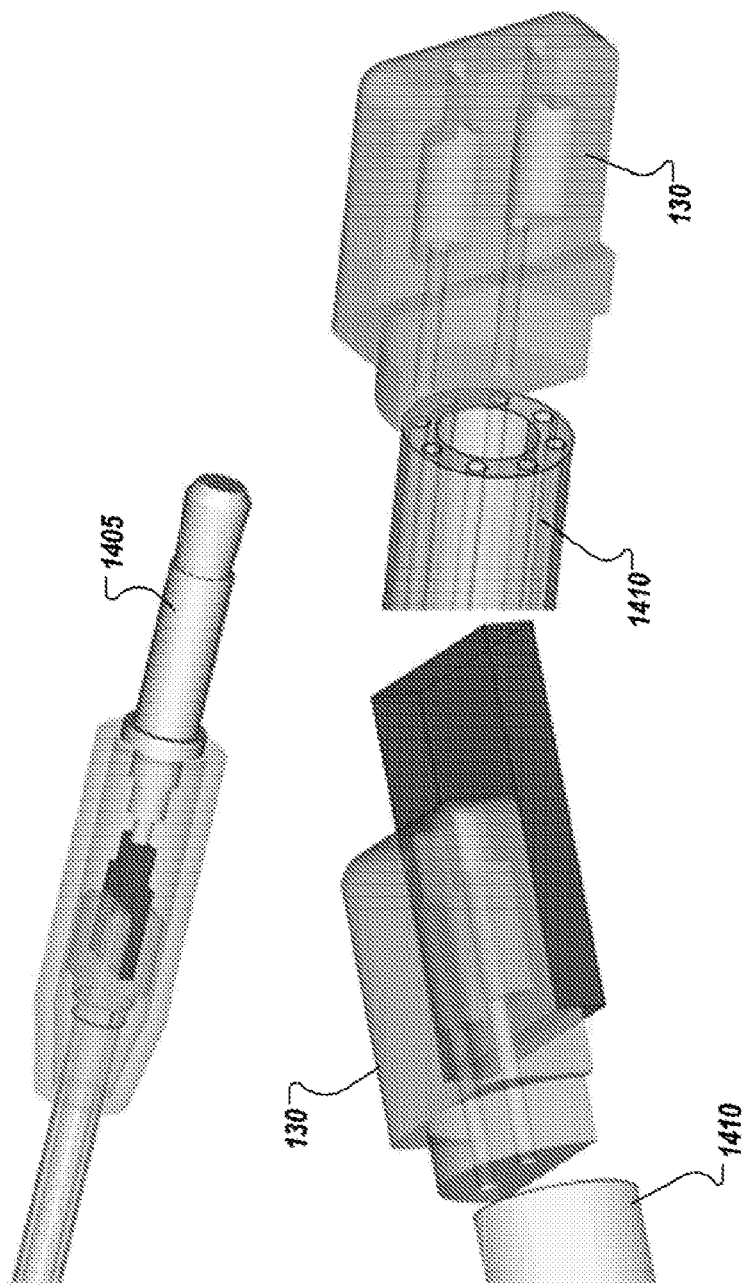
FIG. 14 illustrates simplified schematic diagrams of views of another example connector element.

An example of an electrical component coupled to a fluidic wire by an inline connector element is shown in FIG. 13. In this example, the electrical components are attached to fabric (e.g., of a garment, furniture, etc.) and a liquid metal wire is interwoven with the garment. More specifically, FIG. 13 shows example implementations of in-line components that include LED circuitry connected in line in an example fluidic wire. For instance, in FIG. 13, a view 1305 is shown of the bottom of the fabric showing the connection of interface housing with the conductive liquid filled tubing. Further, a top view 1310 is illustrated of the fabric showing the LED circuitry, with view 1315 showing of the illuminated LEDs (facilitated through inline connections with the fluidic wires).

As introduced in the examples of FIGS. 4-6, endpoint connector components of any one of a variety of different technologies may be coupled to an example fluidic wire by a reservoir-based connector element. FIGS. 14-21 illustrate additional example endpoint connectors, which may utilize liquid metal connections, comparable to the alternative implementations shown and described in the examples of FIGS. 4-6, but without the hollow pins shown and described earlier. For instance, in the example of FIG. 14, rather than using hollow conduit pins to attach the housing for interfacing the PCB with a fluidic wire cable, the fluidic wire may be bonded directly to the housing (e.g., of a connector 130 to connect a 3.5 mm audio jack 1405 to a multi-wire fluidic wire casing (e.g., 1410). Liquid metal leaks from the wire into channels provided in the connector to align with electrical terminations of the metal connector.

Figure 16:
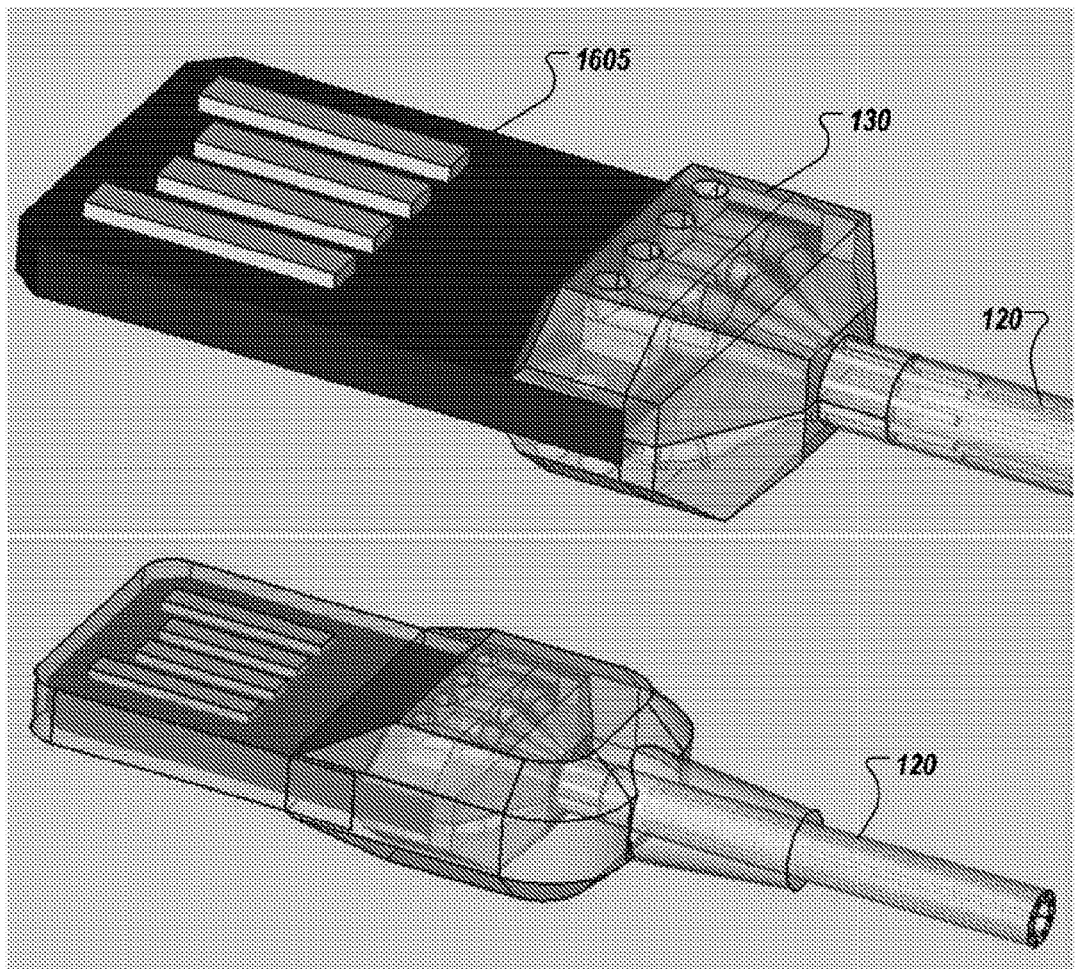
Figure 17:
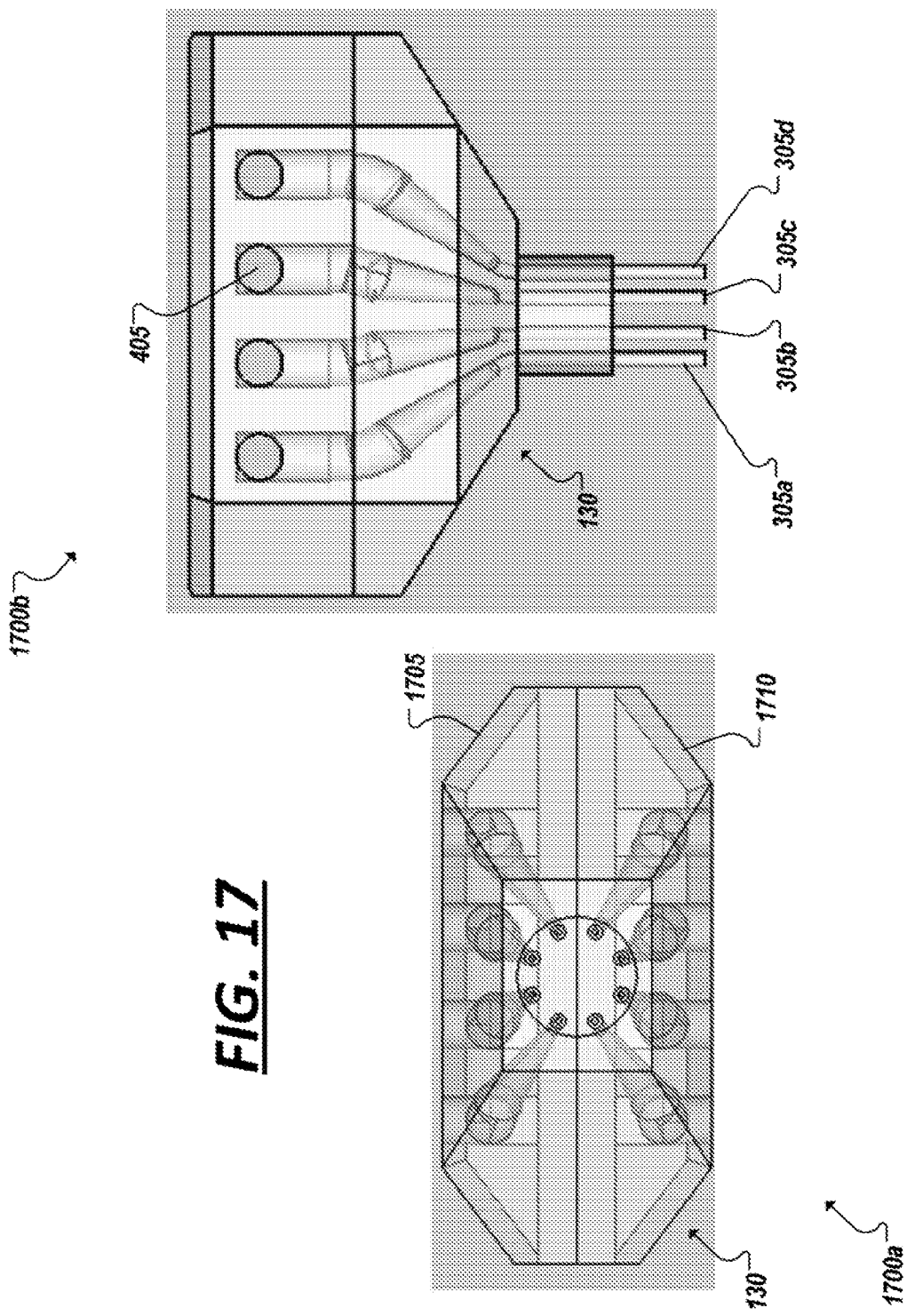
Figure 18:
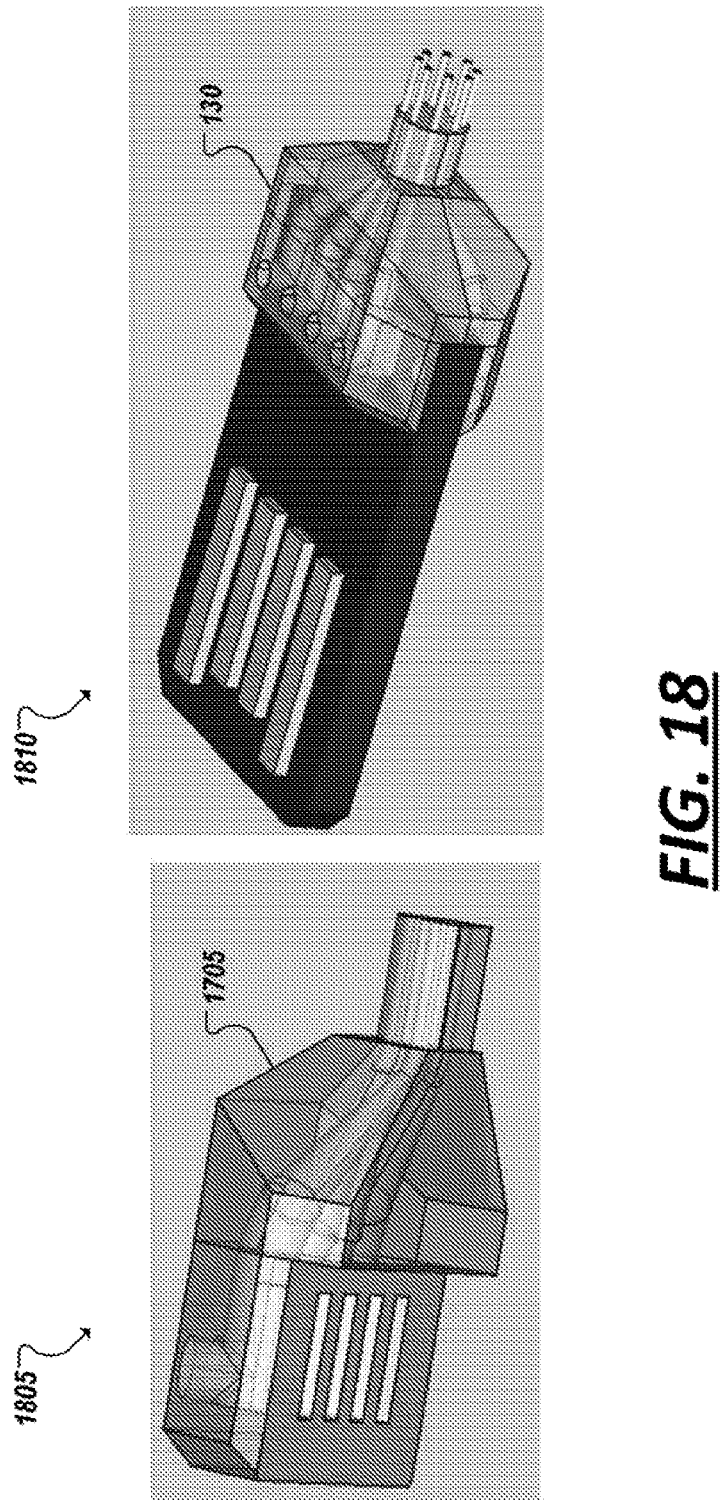

FIGS. 15-18 show views of an example USB-A connector 1505 with an overmolded plastic outer that encases a fluidic wire connector element 130 providing reservoir channels to enable liquid metal from connecting fluidic wires 120 to enter the channels and interface with the metal contacts of the connecter. FIG. 15 shows the connector with the overmolded plastic outer (with transparent view 1510 showing the presence of reservoir-based connector element 130), while FIG. 16 shows the example USB-A connected with the overmolding removed to expose a PCB (1605), fluidic wire connector (130), and multi-lumen fluidic wire cable (120). FIG. 17 shows isolated views 1700a,b of the fluidic wire connector element 130 (implemented in this example in two halves (e.g., 1705, 1710). In this example, eight conduits (e.g., 305a-d) are provided over which fluidic wire lumens (or wire casings) may be connected, to allow liquid metal to reach and contact conductive pads of an electronic component (e.g., PCB) integrated or otherwise connected to the connector element 130. Openings (e.g., 405) are also provided for each signal on the outer section of each half 1705, 1710 for inserting a syringe or other filling device to fill the connected system (e.g., wire casings and connector elements) with liquid metal (e.g., eGaIn). In this example, the reservoirs within the connector element 130 may be open rectangular prisms allowing for liquid metal (e.g., eGaIn) to interface with conductive (e.g., gold-plated) pads corresponding to the associated electronic component. These open sections are part of hollow conduit channels that enter the hollow lumens within the fluidic wire tubing, that are to be filled with eGaIn (or other liquid metal). To complete the assembly, sealing around each open conduit and wire casing tubing can be performed prior to filling and within each outer opening (e.g., 405) (e.g., using UV-curing liquid polymer) to avoid leaking of liquid metal, among other example techniques. FIG. 18 shows a view 1805 of one half 1705 of the fluidic wire connector element 130 shown in FIG. 17, and view 1810 shows the finished connector element 130 with both connector halves, with a corresponding electronic component (e.g., a PCB) coupled to the connector element 130.

Figure 20:
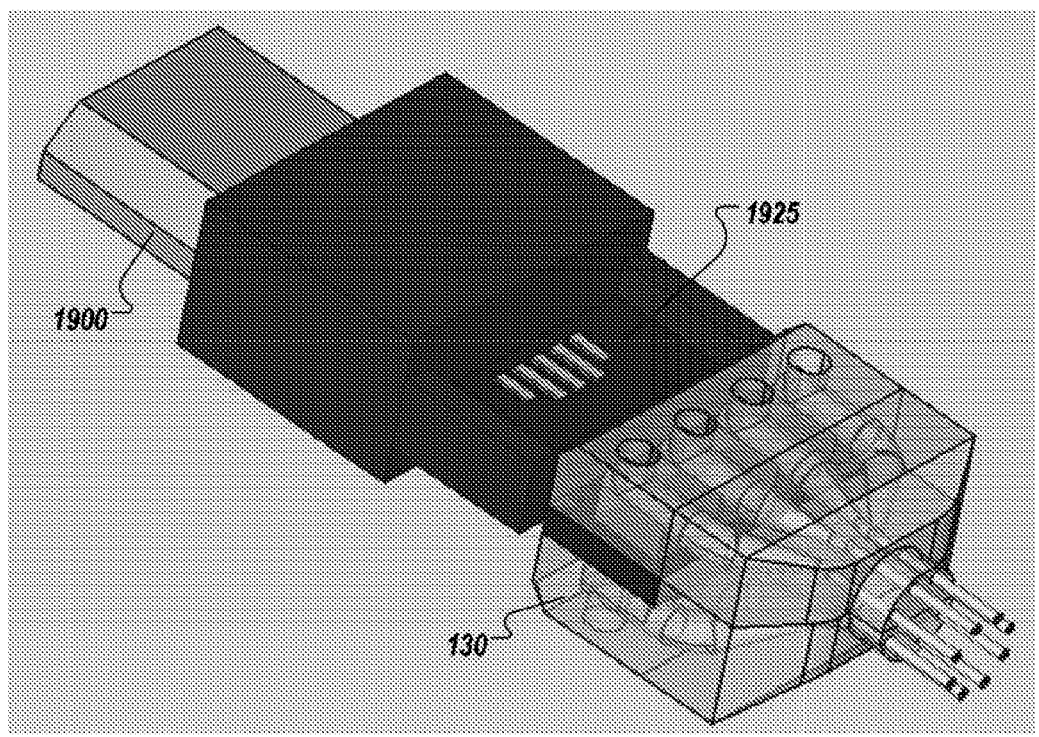

FIG. 19 shows another example implementation, which may include an implementation of a reservoir-based connector element similar to the examples of FIGS. 15-18 to correspond to an electronic device and fluidic wires adapted for another different application, such as a USB-B connector 1900. For instance, the views of FIG. 19 show front and side views of both a full example connector (e.g., views 1905 and 1910 respectively), and similar views (e.g., views 1915 and 1920 respectively) with the overmolding removed to expose views of a PCB, connector element (130), and multi-lumen cable (120). FIG. 20 shows another view, illustrating the addition of a connector device to the PCB and connector element 130, such as a standard SMT Micro USB B male connector 1900. In one example, a 0.8 mm PCB is used to mount the connector device 1900, the PCB integrated with or otherwise connected to the connector element 130 to allow the PCB's 1 mm×2 mm gold-plated pads to interface with liquid metal in corresponding reservoirs provided in the connector element 130 adapted for use with the PCB 1925, such as in at least some of the other examples described herein.

FIG. 21 shows an example of a fluidic wire cable casing 2100, composed of multiple, separate channels or lumens, which may each receive corresponding liquid metal to implement a respective wire in each channel (e.g., 2105, 2110, 2115, etc.) of the cable. For instance, in the example of FIG. 21, a 0.5 mm outside diameter multi-lumen tubing is implemented for use with liquid metal, the cable providing two of the channel (e.g., 2105, 2110, 2115, etc.) per signal. In this example, each lumen channel is 0.3 mm in diameter, with a 1.5 mm center channel 2120 for integrating a stretch-limiting elastomeric cord, braid, or band, among other example features. It should be appreciated that the configuration illustrated in FIG. 21 is for illustration purposes and illustrates one of potentially limitless varieties of cable casing configurations. Cable casing may be configured with a cross-section that is adapted to align with and connect to a configuration of conduits on a reservoir-based connector element (e.g., of a corresponding electronic device). As shown in the example of FIG. 21, multiple fluidic wires may be implemented using multiple channels provided in a single cable casing (e.g., 2100). Further, some of the channels may be utilized to carry other non-fluidic wires, structural elements (e.g., stretch-limiting cords), devices, or other components in addition to other channels adapted for carrying liquid metal to implement liquid wires within the casing, among other example implementations.

Figure 22A:
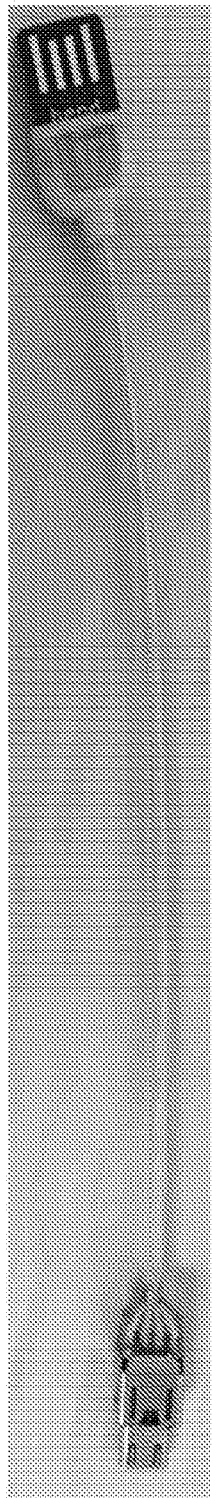
FIGS. 22A-22D are photographs of example components of example systems utilizing liquid metal wires.
Figure 22B:
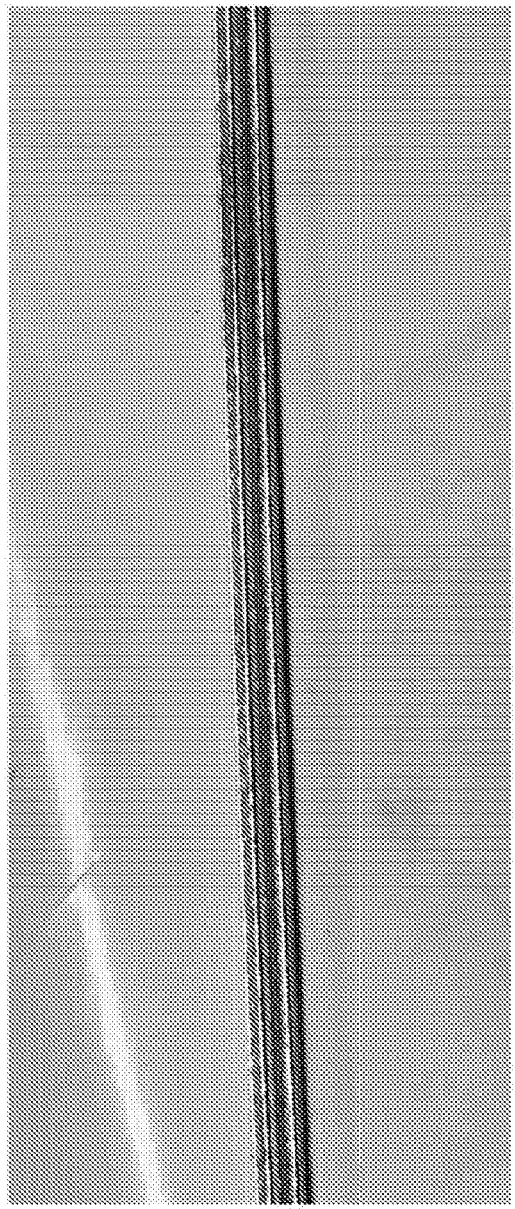
Figure 22D:
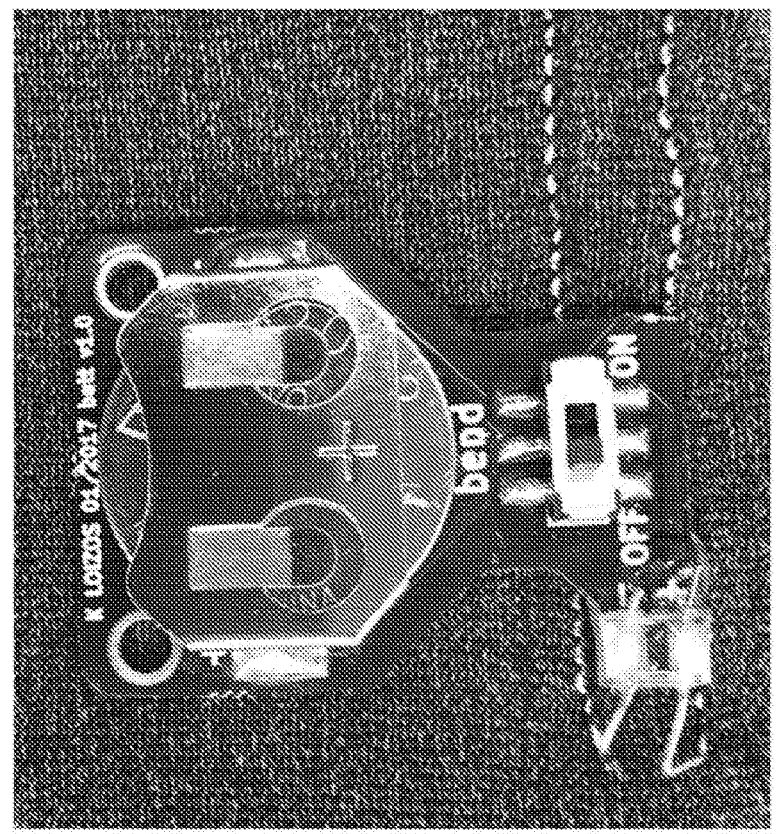
Figure 22C:
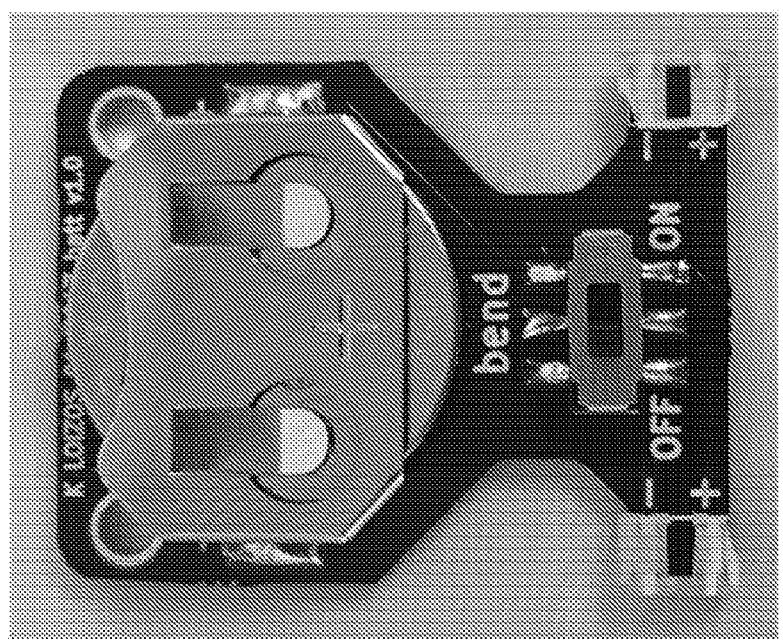

FIGS. 22A-22D show photographs 2200a-d of example implementations of cables with connectors utilizing principles such as described above. For instance, FIG. 22A is a photograph 2200a showing an example prototype of a liquid metal USB-A to micro-B cable. FIG. 22B shows an example liquid metal cable tubing filed with liquid metal (in this case eGaIn). FIGS. 22C-22D show photographs 2200c-d of additional example implementations, such as an implementation of a battery housing component that includes a reservoir-based connector to allow the component to connect in-line with a fluidic wire (shown in FIG. 22D) that is woven into a fabric (e.g., of a garment), among other examples.

Figure 23:
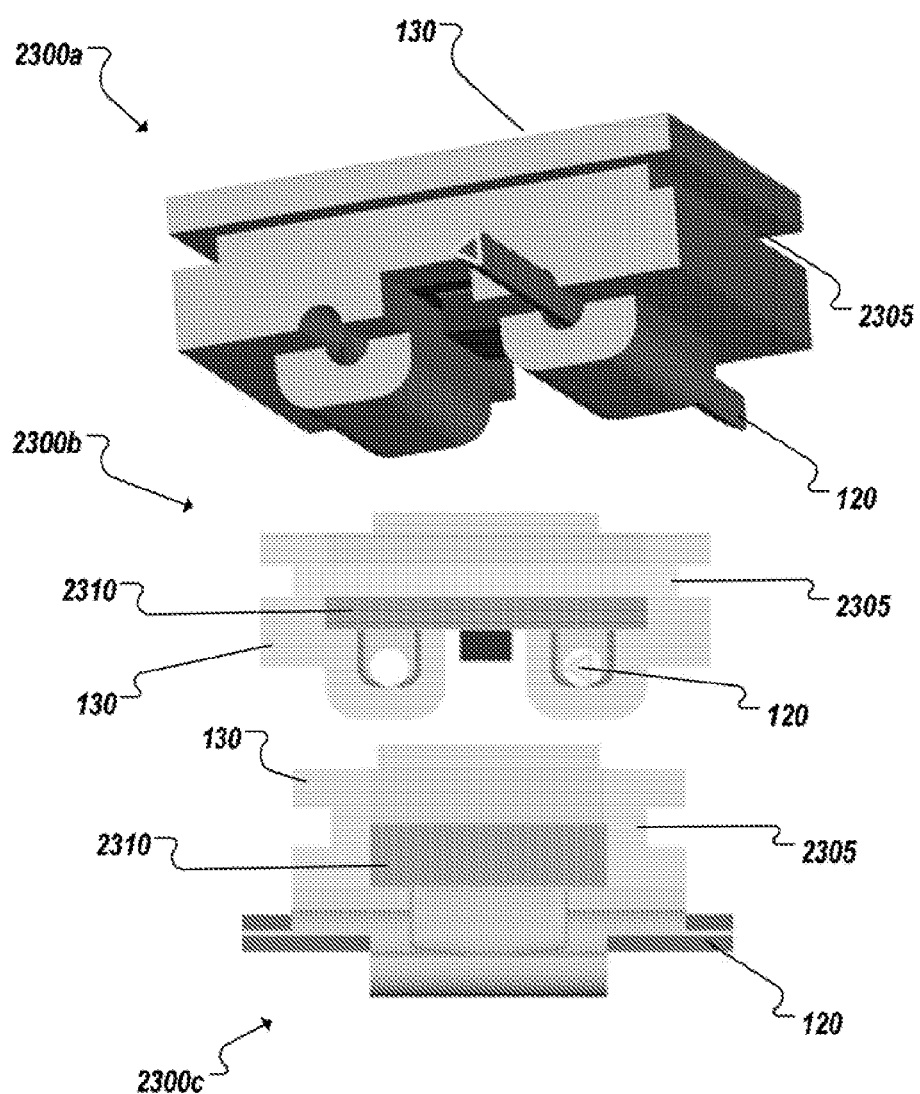
FIG. 23 illustrates simplified schematic diagrams of views of another example connector element.

Turning to FIG. 23, perspective 2300a, front cross-sectional 2300b, and side cross-sectional 2300c views are shown of another implementation of an example reservoir-based connector element 130. In some applications, fluidic wires may be used to connect devices that are to be connected to fabric or another thin substrate to which the fluidic wire is attached or interwoven. In one example, to limit the projection of the device on one or both sides of the substrate, a two-piece connector element (e.g., similar to the embodiments shown in the example of FIG. 12A) may be provided, that is adapted to be positioned through a hole in the substrate, with a top piece of the connector provided on one side of the substrate and the bottom piece of the connector on the other side of the substrate, such that when the two pieces are brought together to assemble the connector element and, at the same time, fasten to the substrate (e.g., in a rivet-like manner). Accordingly, in the particular example shown in FIG. 23, a recessed groove 2305 may be provided in the assembled connector element in which the substrate may be placed or gather to aid in holding the connector to the fabric. For instance, it may desirable for an electronic component to be fastened to a garment, such that a first side of the component (e.g., a light, button, sensor portion, etc.) is exposed on the exterior of the garment, while other portions of the connector element (e.g., the portion to which a fluidic wire (e.g., 120) connects to the connector element 130, a portion housing a PCB or other circuitry (e.g., 2310)) is hidden on the underside of the garment. A small hole can be provided in the garment through which the connector element (and a corresponding electronic device) may be assembled or passed, with the edge of the fabric framing the hole gripped within the groove 2305 of the connector element, among other example implementations.

Figure 24:
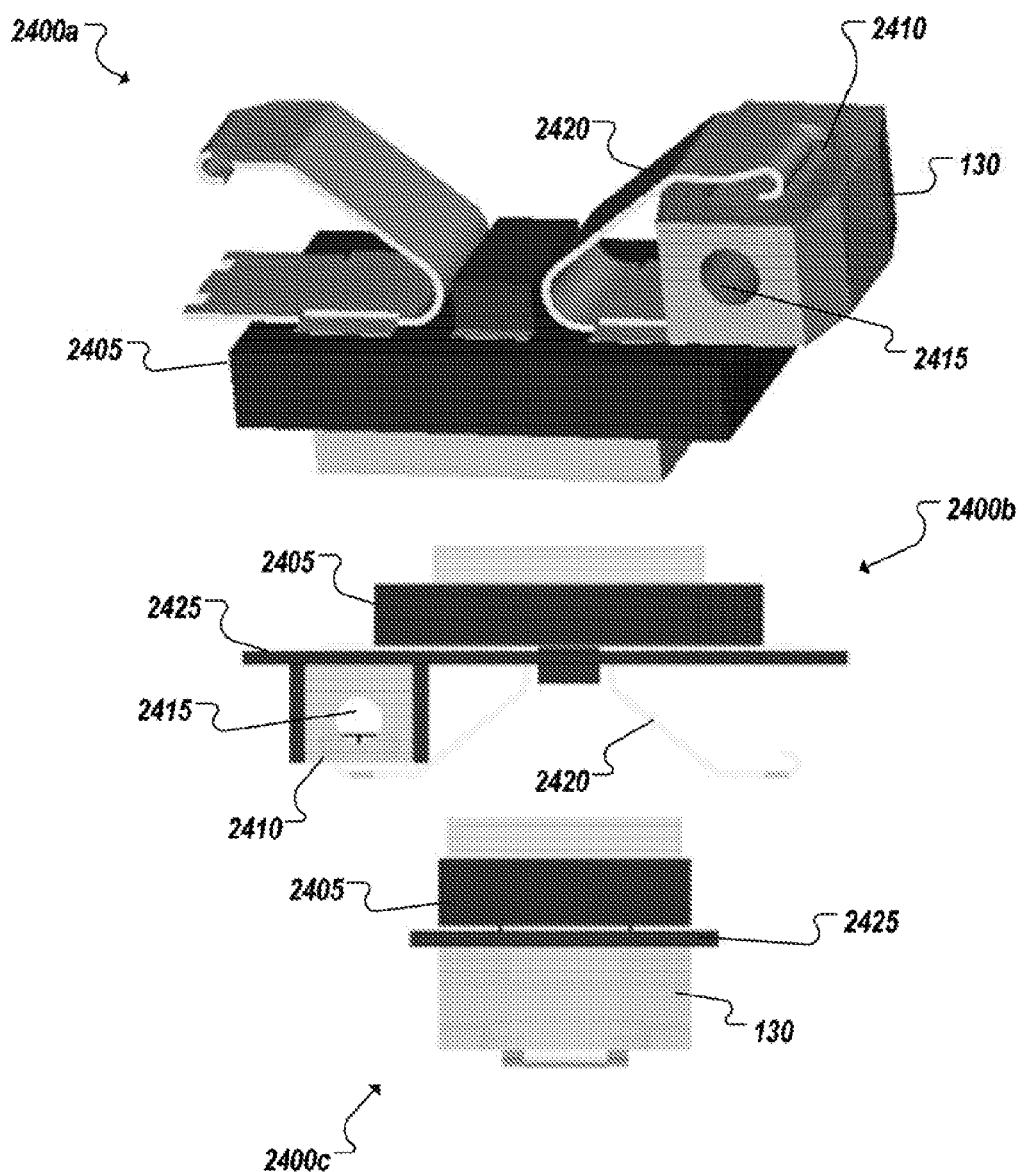
FIG. 24 illustrates a simplified schematic diagram of another example connector element to couple to detachable components.

Turning to the example embodiment illustrated in FIG. 24, perspective 2400a, front 2400b, and side 2400c views are shown of another example implementation to enable detachable device modules (e.g., 2405) from a reservoir-based connector element (e.g., 130). In this example, the connector element 130 may be adapted to connect to a fluidic wire in at least a semi-permanent fashion, such that the connector element 130 may accept various electronic devices (e.g., 2405) which may be effectively "plugged-in" to the connector element 130 in a modular fashion, allowing the connector elements to enjoy the power and/or signaling provided by the fluidic wire(s) connected to the connector. In this particular example, the connector element 130 may expose one or more conductive pads (e.g., 2410) (as in the example of FIG. 10), which may be brought into contact with similar conductive pads on modular electronic devices that are connected to the connector element 130 to establish a connection with the fluidic wire joined to the connector element 130 (e.g., through opening 2415). A variety of mechanisms may be used to physically connect the module device (e.g., 2405) to the connector element 130 to also align the conductive pads of the device 2405 with those (e.g., 2410) of the connector element 130. For instance, in the example of FIG. 24, module devices (e.g., 2405) may be provided with a spring contact 2420 which may both provide a connection to the connector element's solid metal pad 2410 and secure the device 2405 to the connector element 130, as shown in FIG. 24. It should be appreciated that a variety of other similar elements may be utilized either on the connector element or the modular devices to both provide a removable physical and electrical connection between the devices 130, 2405. For instance, while C-shaped springs are shown in the particular example of FIG. 24, it should be appreciated that other spring contacts or other mechanisms may be used, including compression spring contacts, spring-loaded pins, soldered wires, etc. In still some implementations (including that shown in the example of FIG. 24), such spring contacts may not only connect modular devices to connector elements, but may also aid in securing the connector element and electronics to a fabric or other substrate (e.g., 2420), such as in the case of wearable electronics, among other example features.

Figure 25:
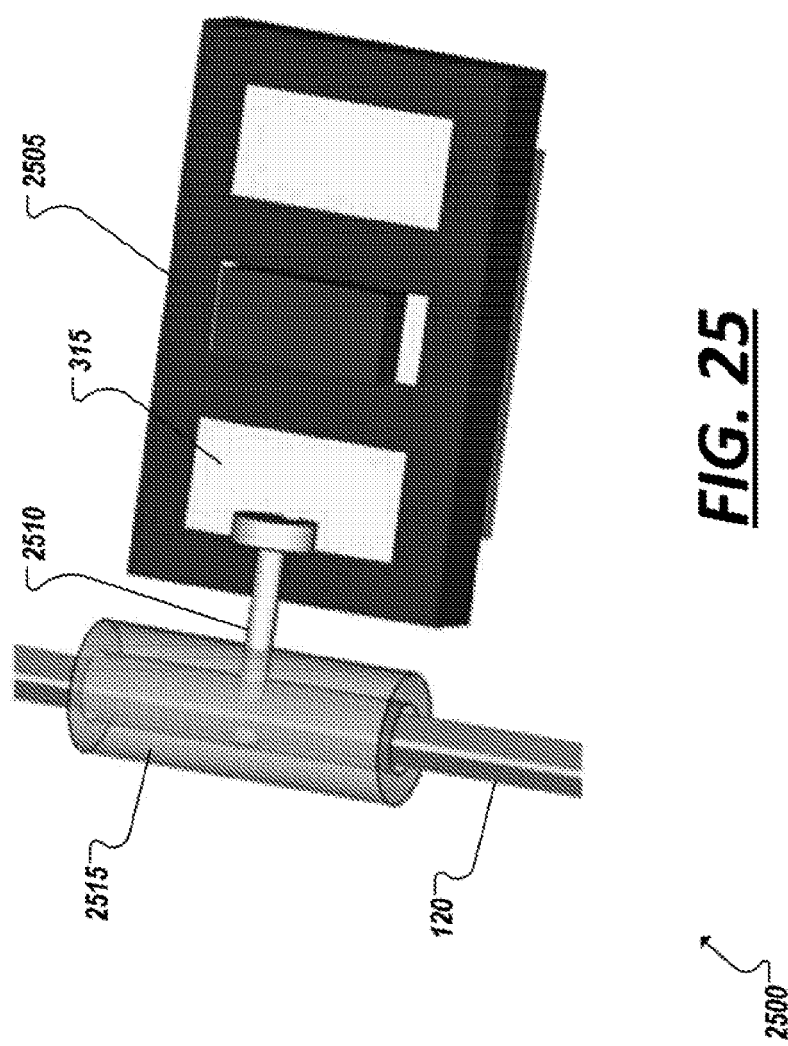
FIG. 25 illustrate a simplified schematic diagram of a solid metal connector to connect to a liquid metal wire through a self-healing surface.

In addition or as an alternative to reservoir-based connector elements, solid-metal connectors may be provided, which may be combined with reservoir-based connector elements in a system, whereby some electronic components are connected to fluidic wires with reservoir-based connector elements while others are connected by solid-metal connectors. In some implementations, a solid-metal connector may be provided to support removable or modular connections of electronic devices to fluidic wires. For instance, in the diagram 2500 of FIG. 25, an example modular electronic device 2505 is shown to include a solid metal pin connector 2510 (extending pad 315), which may be inserted into a fluidic wire (e.g., 120) to be brought into contact with the liquid metal within the wire 120. In this particular example, all or a portion of the liquid metal wire casing may be built from or encased in a self-healing covering 2515 (e.g., made of a self-healing material such as natural rubber or silicone). This allows for components (e.g., 2505) to interface with the liquid metal contained in the fluidic wire(s) 120 by puncturing the wire casing (e.g., before or after filling the wire casing with liquid metal) with a wire, pin, or other solid conductor connector (e.g., 2510). In such examples, the covering, or lining, 2515 serves as a gasket, disallowing liquid metal to exit the system at the location of the puncture. Further, due to the self-healing nature of the covering 2515, a module device (e.g., 2505) may be removed without compromising the wire and another modular device (not shown) may be inserted in its place (e.g., by puncturing the self-healing covering and the encased fluidic wire (e.g., using one or more solid metal connector pins) at the same or a different location used by the previous device (e.g., 2505)), among other example implementations.

Figure 26:
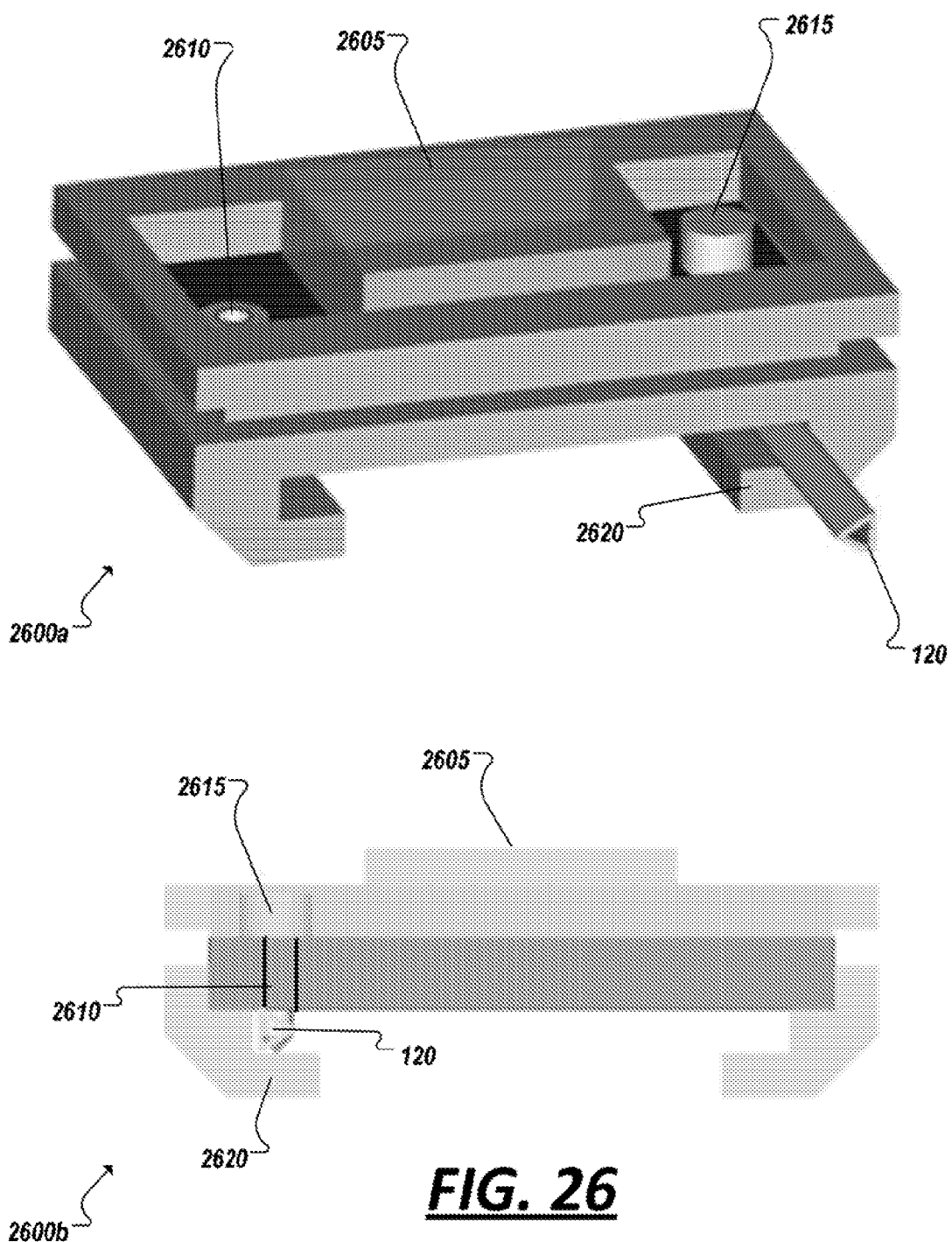
FIG. 26 illustrate a simplified schematic diagram of a solid metal connector to connect to a liquid metal wire through a via.

Turning to the example of FIG. 26, a perspective view 2600a and side view 2600b of another example implementation of a pin-based connector is shown. In this example, an electronic component (e.g., 2605) may be provided with conductive vias (e.g., 2610), through which a solid metal pin or screw 2615 may be passed to puncture a fluidic wire (e.g., 120) positioned beneath the via opening. The solid metal connector 2615 may thereby come into contact with the liquid metal of the fluidic wire and form a connection between the fluidic wire and circuitry of the component 2605 connected to the via conductor. To seal the puncture created in the fluidic wire 120 by the pin or screw 2615, a self-healing covering may be provided on the surface of the wire covering that is to be punctured. In other implementations, another form of gasket, the threads of the screw 2615, or a thread locking compound deposited on the screw 2615 or the exterior of the fluidic wire casing may be used to seal or enhance sealing of the puncture. Further, in some instances, a pin or screw 2615 used to puncture the fluidic wire and provide an electrical connection to an electronic device 2605 may also serve to physically secure the electronic device to the wire (e.g., by pinning the wire 120 to another surface (e.g., 2620)), such as shown in the example of FIG. 26.

Figure 27A:
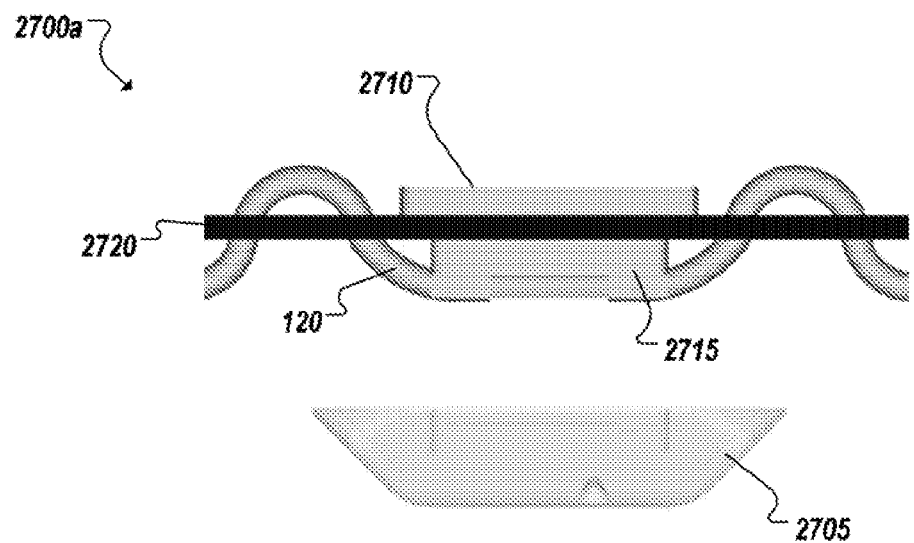
FIGS. 27A-27B illustrate simplified schematic diagrams of views of another example connector element.

Turning to the examples of FIGS. 27A-28, diagrams 2700a-b, 2800 are shown illustrating another implementation of a connector element. In this example, the connector element is composed of two pieces that are to be combined to assemble a reservoir-based connector element adapted to connect to fluidic wires (e.g., similar to the connector element discussed in connection with FIG. 12A). For instance, as shown in FIG. 27A, a bottom (or hidden) piece 2705 of the connector element may attach to a top piece 2710 which may be attached to or be integrated with an electronic device 2715. In this example, a segment of fabric or other substrate material (e.g., 2720) may be provided, over which the top piece 2710 may be positioned. The bottom piece 2705 may be clipped or otherwise connected to the top piece 2710 to sandwich or pinch the fabric 2720 between the two connector element pieces 2705, 2710 to assemble a connector element and secure the connector element to the fabric 2720. The bottom piece 2705, in some implementations may have rounded edges and a smooth exterior surface to be adapted to be in contact with the skin of the wearer of a wearable device and guard the wearer from direct contact with portions of the connector element, device 2715, or fluidic wires 120, which may be enclosed and covered using the bottom piece 2705.

Figure 27B:
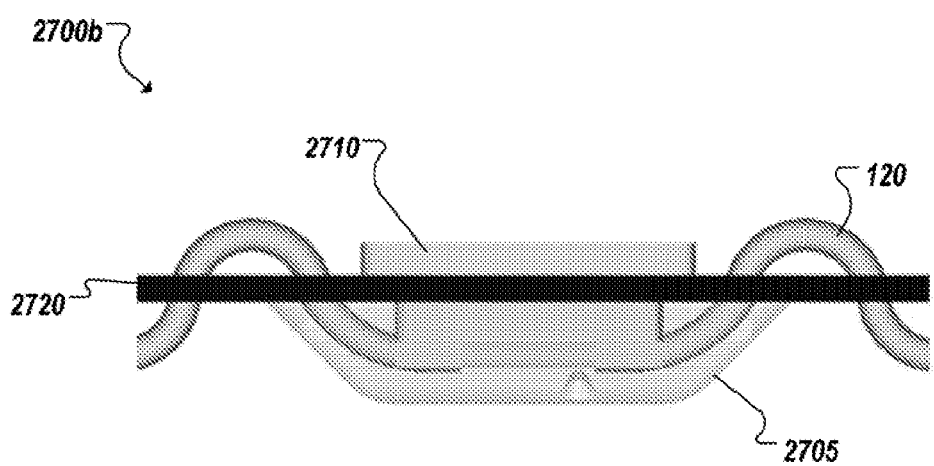

Turning to the examples of FIG. 28, a detailed view 2800 is shown of a portion of a reservoir-based connector element, such as the bottom piece 2705 of the example of FIGS. 27A-27B. In some implementations, a reservoir-based connector element may be provided with small holes (e.g., 2805, 2810), which allow air to escape the connector element while the reservoir and channels of the connector element are being filled with liquid metal. For instance, in some cases, when attaching a connector element to a liquid metal filled fiber (pre- or post-filling), holes (e.g., 2805, 2810) may be added to any locations in which there is a change in the geometry (e.g., the transition from a channel of the fluidic wire or connector conduit to the larger volume of the connector reservoir). This allows air to exit as liquid metal is injected into the system, ensuring that the volume is completely filled with liquid metal. In some instances, the holes 2805, 2810 may be small enough to prevent leakage of liquid metal but to allow the escape of air from the reservoir of the connector element. In other instances, the holes 2805, 2810 may be sealed closed following the filling of the system with liquid metal, among other example implementations.

Figure 29A:
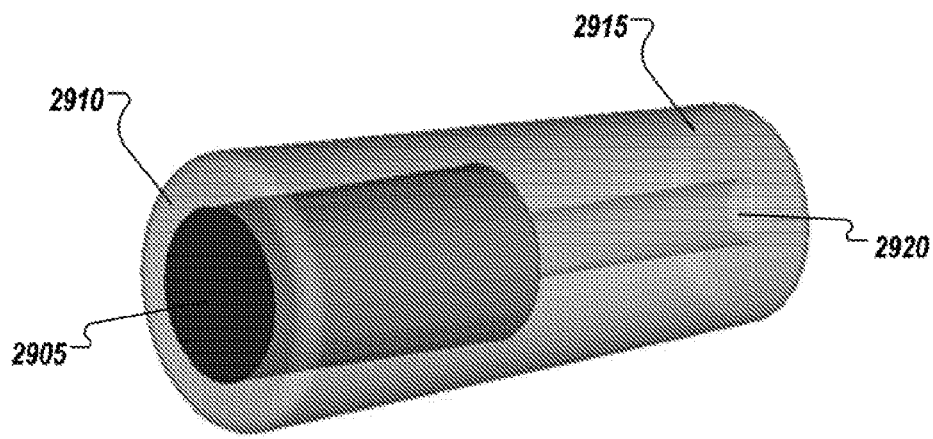
FIGS. 29A-29B illustrate a casing for liquid metal wires including a cap made from self-healing material.
Figure 29B:
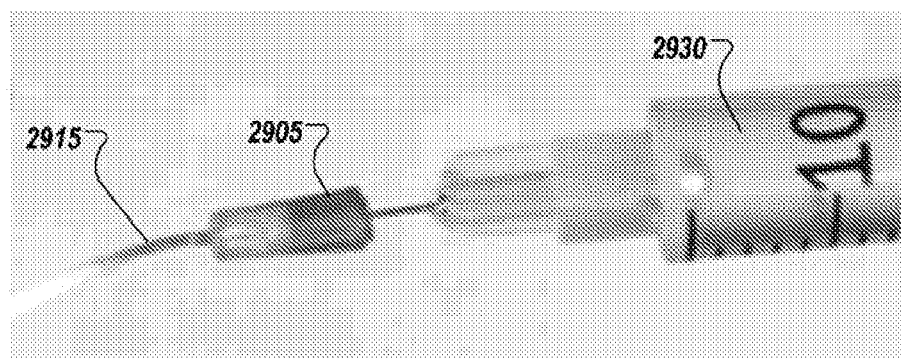

In some instances, it may be challenging to seal the openings (e.g., inlet(s) and outlet(s) of a fluidic wire casing before and after filling the wire casing channel(s) with liquid metal. As illustrated in the example of FIGS. 8-9, one approach is to provide a hollow pin that may be crimped following filling to seal an end of the wire casing channel. In another approach, illustrated in the examples of FIGS. 29A-29B, a self-healing compound (e.g., 2905), such as natural rubber, may be provided at the inlet(s) and outlet(s) (e.g., 2910) of the wire casing (e.g., 2915) to serve as a gasket. The self-healing matter may form a cap at the terminal openings of the wire casing. As shown in FIG. 29B, a needle (e.g., of a syringe 2930) may then puncture the self-healing compound 2905, allowing access to the internal section 2920 of the system such that liquid metal may be injected or air evacuated from the system. The self-healing cap 2905 may thereby serve as a seal during filling, disallowing liquid metal to exit the system in undesired locations. The self-healing properties of the rubber may further allows needle(s) to be removed at any time without causing liquid metal to exit the system, or otherwise modifying the internal pressure or volume of the system, among other example features and advantages.

Self-healing material may also be provided on reservoir-based connector elements, in some implementations. For instance, as shown in the example of FIGS. 30A-30B, openings (e.g., the openings 405 shown in the example connector element of FIG. 4) may be replaced or covered using self-healing material. For instance, FIG. 30A shows a bottom cross-sectional view of an example connector element 130, with channels 3005, 3010 permitting liquid metal to be injected into reservoirs of the connector element to bring liquid metal into contact with solid metal contacts (e.g., 3015, 3020) of an example device 3035. In this example, the openings of channels 3005, 3010 may be covered by caps 3025, 3030 made of self-healing material. A syringe needle may thereby be inserted into the caps 3025, 3030 to deposit liquid metal in the connector element without risk of liquid metal leaking from the openings. FIG. 30B shows a perspective view of the example connector element shown and described in FIG. 30A.

Reference throughout this specification to "one implementation" or "an implementation" means that a particular feature, structure, or characteristic described in connection with the implementation is included in at least one implementation of the present invention. Thus, the appearances of the phrases "in one implementation" or "in an implementation" in various places throughout this specification are not necessarily all referring to the same implementation. Furthermore, the particular features, structures, or characteristics may be combined in any suitable manner in one or more implementations.

The following examples pertain to embodiments in accordance with this Specification. Example 1 is an apparatus including: a connector including: a hollow conduit configured to connect to a tubular wire casing; and a reservoir including a solid metal conductor, where the reservoir is to receive liquid metal to substantially fill a volume of the reservoir, the liquid metal extends into the tubular wire casing, where the tubular wire casing, when filled with the liquid metal, includes a liquid metal wire.

Example 2 may include at least a portion of the subject matter of example 1, where the conduit protrudes from an exterior surface of the connector.

Example 3 may include at least a portion of the subject matter of example 2, where the conduit is to be inserted into an opening of the wire casing to connect to the wire casing.

Example 4 may include at least a portion of the subject matter of example 2, where the wire casing is to be inserted into an opening of the conduit to connect the conduit to the wire casing.

Example 5 may include at least a portion of the subject matter of any one of examples 2-4, where cross-sectional geometry of the wire casing corresponds to cross-sectional geometry of the conduit.

Example 6 may include at least a portion of the subject matter of any one of examples 1-5, where the conductor includes at least a portion of the surface of the reservoir.

Example 7 may include at least a portion of the subject matter of any one of examples 1-6, where the conduit is sealed to the tubular wire casing to form a continuous volume within the tubular wire casing and reservoir.

Example 8 may include at least a portion of the subject matter of any one of examples 1-7, where the connector further including an opening to accept injection of the liquid metal into the reservoir.

Example 9 may include at least a portion of the subject matter of example 8, where the opening includes a cap made of self-healing material.

Example 10 may include at least a portion of the subject matter of any one of examples 1-9, further including an electronic device coupled to the connector, where the conductor is to provide an electrical connection from the liquid metal to the electronic device.

Example 11 may include at least a portion of the subject matter of example 10, where the electronic device includes the connector.

Example 12 may include at least a portion of the subject matter of any one of examples 10-11, where the electronic device includes a particular connector to connect to another device.

Example 13 may include at least a portion of the subject matter of example 12, where the particular connector is one of a Universal Serial Bus (USB) connector, audio jack, Lightning connector, or High Definition Multimedia Interface (HDMI) connector.

Example 14 may include at least a portion of the subject matter of example 13, where the particular connector is to connect to a set of liquid metal wires corresponding to a cable for sending signals corresponding to the particular connector.

Example 15 may include at least a portion of the subject matter of example 12, where the particular connector includes a connector for a power cable, where the power cable includes the liquid metal wire.

Example 16 may include at least a portion of the subject matter of example 10, where the electronic device includes one of a processor, sensor, actuator, memory element, antennae, or user interface device.

Example 17 may include at least a portion of the subject matter of any one of examples 1-16, where the connector further includes: a plurality of conduits including the conduit; and a plurality of reservoirs including the reservoir, where each of the plurality of conduits is to connect a respective liquid metal wire to a respective one of the plurality of reservoirs, and each of the plurality of reservoirs includes a respective conductor.

Example 18 may include at least a portion of the subject matter of any one of examples 1-17, where the connector is adapted to accept and conductively couple to a detachable electronic device.

Example 19 may include at least a portion of the subject matter of example 18, where the connector includes a conductive pad to be brought into contact with a conductor of the detachable electronic device.

Example 20 may include at least a portion of the subject matter of example 19, where the connector includes means to physically secure the detachable electronic device to the connector.

Example 21 may include at least a portion of the subject matter of example 19, where the detachable electronic device includes means to physically secure the detachable electronic device to the connector.

Example 22 may include at least a portion of the subject matter of example 21, where the means include a conductive clip, and the conductive clip includes the conductor of the detachable electronic device.

Example 23 may include at least a portion of the subject matter of any one of examples 1-22, where the connector includes a recess on at least one side of the connector to accept a layer of substrate to be in contact with the connector on the at least one side.

Example 24 may include at least a portion of the subject matter of example 23, where the recess includes a recess around a perimeter of the connector to accept the layer of the substrate when the connector is passed through an opening in the substrate.

Example 25 may include at least a portion of the subject matter of any one of examples 23-24 where the substrate includes fabric.

Example 26 may include at least a portion of the subject matter of example 25, where the fabric includes one of upholstery fabric or fabric of a wearable device.

Example 27 may include at least a portion of the subject matter of any one of examples 1-26, where the connector includes a hole to allow escape of air while liquid metal flows into the reservoir.

Example 28 is a method including: inserting one or more conduits of a connector into a cable casing, where the connector includes one or more reservoirs corresponding to the one or more conduits, each of the one or more reservoirs includes a respective solid metal conductor, and the one or more reservoirs when filled with liquid metal bring the liquid metal into conduct with the conductor of the reservoir; and injecting liquid metal to fill a channel of the cable casing and the one or more reservoirs, where the liquid metal passes between the channel of the cable casing and the one or more reservoirs via the one or more conduits.

Example 29 may include at least a portion of the subject matter of example 28, further including sealing the cable casing to the connector.

Example 30 may include at least a portion of the subject matter of example 28, where the cable casing includes a first opening at a first end of the cable and a second opening at a second end of the cable, the connector includes a first connector, and the conduit of the first connector is inserted into the cable casing using the first opening, and the method further includes: inserting a conduit of a second connector into the second opening of the cable casing to connect the second connector to the cable casing, where the second connector includes a reservoir and connecting the second connector to the cable casing forms a continuous volume including an inner channel of the cable casing, the reservoir of the first connector, and the reservoir of the second connector.

Example 31 may include at least a portion of the subject matter of any one of examples 28-30, where the liquid metal includes eutectic gallium indium (EGaIn).

Example 32 is an apparatus including: a first electronic component coupled to a first connector; a second electronic component coupled to a second connector; and a liquid metal wire connecting the first connector to the second connector, where the first connector includes: a hollow conduit configured to connect to a tubular casing of the liquid metal wire; and a reservoir including a solid metal conductor, where the reservoir is to be substantially filled with liquid metal extending into the liquid metal wire to bring the liquid metal into contact with the solid metal conductor, and the solid metal conductor is conductively connected to circuitry of the first electronic component.

Example 33 may include at least a portion of the subject matter of example 32, where the second connector includes: a hollow conduit configured to connect to the tubular casing of the liquid metal wire; and a reservoir including a solid metal conductor, where the reservoir of the second connector is to be substantially filled with liquid metal extending into the liquid metal wire to bring the liquid metal into contact with the solid metal conductor of the second connector, and the solid metal conductor of the second connector is conductively connected to circuitry of the second electronic component.

Example 34 may include at least a portion of the subject matter of any one of examples 32-33, where the first connector is coupled in-line with the liquid metal wire.

Example 35 may include at least a portion of the subject matter of any one of examples 32-34, where the apparatus includes a wearable device.

Example 36 may include at least a portion of the subject matter of any one of examples 32-35, where the first connector is adapted to accept and conductively couple to a detachable electronic device and the first electronic component includes a detachable electronic device.

Example 37 may include at least a portion of the subject matter of example 36, where the first connector includes a conductive pad to be brought into contact with a conductor of the detachable electronic device.

Example 38 may include at least a portion of the subject matter of example 37, where the first connector includes means to physically secure the detachable electronic device to the first connector.

Example 39 may include at least a portion of the subject matter of example 37, where the detachable electronic device includes means to physically secure the detachable electronic device to the first connector.

Example 40 may include at least a portion of the subject matter of example 39, where the means include a conductive clip, and the conductive clip includes the conductor of the detachable electronic device.

Example 41 may include at least a portion of the subject matter of any one of examples 32-40, where the first connector includes a recess on at least one side of the first connector to accept a layer of substrate to be in contact with the first connector on the at least one side.

Example 42 may include at least a portion of the subject matter of example 41, where the recess includes a recess around a perimeter of the first connector to accept the layer of the substrate when the first connector is passed through an opening in the substrate.

Example 43 may include at least a portion of the subject matter of any one of examples 41-42, where the substrate includes fabric.

Example 44 may include at least a portion of the subject matter of example 43, where the fabric includes one of upholstery fabric or fabric of a wearable device.

Example 45 may include at least a portion of the subject matter of any one of examples 32-44, where the first connector includes a hole to allow escape of air while liquid metal flows into the reservoir.

Example 46 is an apparatus including: a fluidic wire casing, where the fluidic wire is made of elastomeric material and includes a plurality of channels, where each of the plurality of channels includes a respective inlet and outlet, each of the plurality of channels is to receive liquid metal through the inlet of the channel, and each of the plurality of channels is to implement a liquid metal wire when filled with the liquid metal.

Example 47 may include at least a portion of the subject matter of example 46, where the fluidic wire casing is stretchable and liquid metal wires implemented using the fluidic wire casing are stretchable.

Example 48 may include at least a portion of the subject matter of any one of examples 46-47, where the inlets of the plurality of channels are physically arranged according to a particular cross-sectional layout.

Example 49 may include at least a portion of the subject matter of example 48, where the particular cross-sectional layout corresponds to a layout of conduits of a connector element and the fluidic wire casing is adapted to connect to the connector element at the conduits.

Example 50 may include at least a portion of the subject matter of example 49, where connecting the fluidic wire casing to the connector element includes inserting the conduits of the connector element into at least a portion of the inlets of the plurality of channels.

Example 51 may include at least a portion of the subject matter of any one of examples 49-50, where the connector element includes a first connector element to facilitate an electrical connection to a first electronic device, and the outlets of the plurality of channels are to connect to conduits of a second connector element facilitating an electrical connection to a second electronic device.

Example 52 may include at least a portion of the subject matter of any one of examples 46-51, where the plurality of channels includes a particular number of channels to implement a cable including the particular number of liquid metal wires.

Example 53 may include at least a portion of the subject matter of example 52, where the particular number of liquid metal wires corresponds to a number of wires to implement signals of a particular protocol.

Example 54 may include at least a portion of the subject matter of claim 53, where the particular protocol includes one of a USB-based protocol, an HDMI protocol, a Peripheral Interconnect Express (PCIe) protocol, or Ethernet protocol.

Example 55 may include at least a portion of the subject matter of any one of examples 46-54, further including a channel to at least partially contain a stretch-limiting cord.

Example 56 may include at least a portion of the subject matter of any one of examples 46-55, where at least a particular one of the plurality of channels includes a rectangular cross-sectional geometry.

Example 57 may include at least a portion of the subject matter of any one of examples 46-55, where at least a particular one of the plurality of channels includes a cylindrical geometry.

Example 58 may include at least a portion of the subject matter of any one of examples 46-55, where at least a particular one of the plurality of channels includes a triangular cross-sectional geometry.

Example 59 may include at least a portion of the subject matter of example 42, where the liquid metal wire includes the fluidic wire casing of any one of examples 46-58.

Example 60 is a method to manufacture a liquid metal wire, including injecting liquid metal into at least some of the plurality of channels of the fluidic wire casing of any one of examples 46-58.

Example 61 may include at least a portion of the subject matter of example 60, further including sealing the inlet and outlet of the at least some of the plurality of channels.

Example 62 may include at least a portion of the subject matter of example 61, where the inlets and outlets of the sealed plurality of channels are sealed using a self-healing material.

Example 63 is an apparatus including: a connector including: a first connector section; and a second connector section to coupled to the first section to form the connector, where the connector includes a conduit and an internal reservoir to be filled with liquid metal to extend through the conduit to an opening of a wire casing to house a liquid metal wire, and the reservoir includes a solid metal conductor to contact the liquid metal to complete a circuit including a first component attached to the connector and the liquid metal wire.

Example 64 may include at least a portion of the subject matter of example 63, where the circuit is to further include a second component to be connected to the liquid metal wire.

Example 65 may include at least a portion of the subject matter of any one of examples 63-64, where the first connector and second connector, when coupled together, trap a layer of a substrate between the first and second connector sections to attach the connector to the substrate.

Example 66 may include at least a portion of the subject matter of example 65, where the substrate includes a fabric.

Example 67 may include at least a portion of the subject matter of example 66, where the fabric includes fabric of one of a garment.

Example 68 may include at least a portion of the subject matter of example 66, where the fabric includes upholstery fabric.

Example 69 may include at least a portion of the subject matter of any one of examples 63-68, where the first connector section includes a sharp element to puncture the liquid metal wire to form the opening.

Example 70 may include at least a portion of the subject matter of example 69, where puncturing the liquid metal wire causes liquid metal from the liquid metal wire to leak into the reservoir.

Example 71 may include at least a portion of the subject matter of any one of examples 69-70, where the liquid metal wire is positioned between the first and second connector sections and is punctured during the coupling of the first connector section to the second connector section.

Example 72 may include at least a portion of the subject matter of any one of examples 66-70, where the first connector section is to house at least a portion of an electronic component coupled to the connector.

Example 73 may include at least a portion of the subject matter of any one of examples 66-71, where the first and second connection sections are to be combined to form the connector, the connector includes a plurality of reservoirs to corresponding to a plurality of solid conductors.

Example 74 may include at least a portion of the subject matter of any one of examples 66-73, where the first connection section includes a hole to allow escape of air while liquid metal flows into the reservoir.

Example 75 may include at least a portion of the subject matter of example 74, where the hole is positioned to corresponding to location of the reservoir within the connector.

Example 76 may include at least a portion of the subject matter of any one of examples 66-75, where the connector is adapted to connect to an end of the liquid metal wire.

Example 77 may include at least a portion of the subject matter of any one of examples 66-75, where the connector is adapted to connect in-line to the liquid metal wire, between ends of the liquid metal wire.

Example 78 may include at least a portion of the subject matter of any one of examples 65-77, further including an electronic device to be coupled to the connector.

Example 79 may include at least a portion of the subject matter of any one of examples 65-78, where the connector includes a plurality of conduits and a plurality of reservoirs with a plurality of solid metal conductors to facilitate connection to a corresponding plurality of liquid metal wires.

Example 80 may include at least a portion of the subject matter of any one of examples 65-79, where the connector is adapted to accept and conductively couple to a detachable electronic device.

Example 81 may include at least a portion of the subject matter of example 80, where the connector includes a conductive pad to be brought into contact with a conductor of the detachable electronic device.

Example 82 may include at least a portion of the subject matter of example 81, where the connector includes means to physically secure the detachable electronic device to the connector.

Example 83 may include at least a portion of the subject matter of example 81, where the detachable electronic device includes means to physically secure the detachable electronic device to the connector.

Example 84 may include at least a portion of the subject matter of example 83, where the means include a conductive clip, and the conductive clip includes the conductor of the detachable electronic device.

Example 85 may include at least a portion of the subject matter of any one of examples 65-84, where the connector includes a recess on at least one side of the connector to accept a layer of substrate to be in contact with the connector on the at least one side.

Example 86 may include at least a portion of the subject matter of example 85, where the recess includes a recess around a perimeter of the connector to accept the layer of the substrate when the connector is passed through an opening in the substrate.

Example 87 may include at least a portion of the subject matter of any one of examples 84-85, where the substrate includes fabric.

Example 88 may include at least a portion of the subject matter of example 87, where the fabric includes one of upholstery fabric or fabric of a wearable device.

Example 89 may include at least a portion of the subject matter of any one of examples 65-88, where the connector includes an opening to permit injection of liquid metal into the reservoir.

Example 90 is an apparatus including: a first electronic component coupled to a first connector; a second electronic component coupled to a second connector; and a liquid metal wire connecting the first connector to the second connector, where the first connector includes: a first connector section; and a second connector section to be coupled to the first section to form the connector, where the connector includes a hollow conduit and an internal reservoir to be filled with liquid metal to extend through the conduit to an opening of a wire casing to house a liquid metal wire, and the reservoir includes a solid metal conductor to contact the liquid metal to complete a circuit including a first component attached to the connector and the liquid metal wire.

Example 91 may include at least a portion of the subject matter of example 90, where the first connector is coupled in-line with the liquid metal wire.

Example 92 may include at least a portion of the subject matter of any one of examples 90-91, where a cross-sectional geometry of the wire casing corresponds to a cross-sectional geometry of the conduit.

Example 93 may include at least a portion of the subject matter of any one of examples 90-92, where the apparatus includes a wearable device.

Example 94 may include at least a portion of the subject matter of any one of examples 90-93, where the first connector is adapted to accept and conductively couple to a detachable electronic device.

Example 95 may include at least a portion of the subject matter of example 94, where the first connector includes a conductive pad to be brought into contact with a conductor of the detachable electronic device.

Example 96 may include at least a portion of the subject matter of example 95, where the first connector includes means to physically secure the detachable electronic device to the first connector.

Example 97 may include at least a portion of the subject matter of example 95, where the detachable electronic device includes means to physically secure the detachable electronic device to the first connector.

Example 98 may include at least a portion of the subject matter of example 96, where the means include a conductive clip, and the conductive clip includes the conductor of the detachable electronic device.

Example 99 may include at least a portion of the subject matter of any one of examples 90-98, where the first connector includes a recess on at least one side of the first connector to accept a layer of substrate to be in contact with the first connector on the at least one side.

Example 100 may include at least a portion of the subject matter of example 99, where the recess includes a recess around a perimeter of the first connector to accept the layer of the substrate when the first connector is passed through an opening in the substrate.

Example 101 may include at least a portion of the subject matter of any one of examples 99-100, where the substrate includes fabric.

Example 102 may include at least a portion of the subject matter of example 101, where the fabric includes one of upholstery fabric or fabric of a wearable device.

Example 103 may include at least a portion of the subject matter of any one of examples 90-102, where the first connector includes a hole to allow escape of air while liquid metal flows into the reservoir.

Example 104 is an apparatus including: an electronic device including a conductor to electrically connect the electronic device to another conductor, where the conductor includes a pin projecting from the electronic device; a liquid metal wire including a wire casing to house liquid metal, where at least a portion of the wire casing includes a layer of self-healing material, where the pin punctures the portion of the wire casing to bring the pin into contact with the liquid metal and removably connect the electronic device to the liquid metal wire.

Example 105 may include at least a portion of the subject matter of example 104, where the self-healing material includes one of natural rubber and silicone.

Example 106 may include at least a portion of the subject matter of any one of examples 104-105, where the wire casing includes a base layer to form an interior surface of a channel housing the liquid metal and the layer of self-healing material is on top of the base layer.

Example 107 is an apparatus including: a connector to connect to one or more conductors of an electronic device, where the connector includes: one or more vias, where each of the one or more vias pass through the connector to form a respective hole in the connector and are at least partially lined with a solid metal conductor to electrically couple to the one or more conductors of the electronic device; and a conductive member to pass through one of the vias and penetrate a liquid metal wire to create an electrical connection from the solid metal conductor of the via to liquid metal contained in the liquid metal wire.

Example 108 may include at least a portion of the subject matter of example 107, where the electronic device includes a circuit board mounted on the connector.

Example 109 may include at least a portion of the subject matter of example 108, where the one or more vias penetrate the circuit board.

Example 110 may include at least a portion of the subject matter of any one of examples 107-108, where the conductive member includes a screw.

Example 111 may include at least a portion of the subject matter of any one of examples 107-108, where the conductive member includes a solid pin.

Example 112 may include at least a portion of the subject matter of any one of examples 107-111, where the conductive member is to puncture the liquid metal wire.

Example 113 may include at least a portion of the subject matter of any one of examples 107-112, where the conductive member is to pin the liquid metal wire to a surface of the connector to physically couple the liquid metal wire to the connector.

Example 114 may include at least a portion of the subject matter of any one of examples 107-113, where the connector is adapted to accept and conductively couple to a detachable electronic device.

Example 115 may include at least a portion of the subject matter of example 114, where the connector includes a conductive pad to be brought into contact with a conductor of the detachable electronic device.

Example 116 may include at least a portion of the subject matter of example 115, where the connector includes means to physically secure the detachable electronic device to the connector.

Example 117 may include at least a portion of the subject matter of example 115, where the detachable electronic device includes means to physically secure the detachable electronic device to the connector.

Example 118 may include at least a portion of the subject matter of example 117, where the means include a conductive clip, and the conductive clip includes the conductor of the detachable electronic device.

Example 119 may include at least a portion of the subject matter of any one of examples 107-118, where the connector includes a recess on at least one side of the connector to accept a layer of substrate to be in contact with the connector on the at least one side.

Example 120 may include at least a portion of the subject matter of example 119, where the recess includes a recess around a perimeter of the connector to accept the layer of the substrate when the connector is passed through an opening in the substrate.

Example 121 may include at least a portion of the subject matter of any one of examples 119-120, where the substrate includes fabric.

Example 122 may include at least a portion of the subject matter of example 121, where the fabric includes one of upholstery fabric or fabric of a wearable device.

Example 123 may include at least a portion of the subject matter of any one of examples 107-122, where the connector includes a hole to allow escape of air while liquid metal flows into the reservoir.

Example 124 is an apparatus including: a first electronic component coupled to a first connector; a second electronic component coupled to a second connector; and a liquid metal wire connecting the first connector to the second connector, where the first connector includes: one or more vias, where each of the one or more vias pass through the first connector to form a respective hole in the first connector and are at least partially lined with a solid metal conductor to electrically couple to the one or more conductors of the first electronic device; and a conductive member to pass through one of the vias and penetrate the liquid metal wire to create an electrical connection from the solid metal conductor of the via to liquid metal contained in the liquid metal wire.

Example 125 may include at least a portion of the subject matter of example 124, where the apparatus includes a wearable device.

Example 126 may include at least a portion of the subject matter of any one of examples 124-125, where the first connector is adapted to accept and conductively couple to a detachable electronic device.

Example 127 may include at least a portion of the subject matter of example 126, where the first connector includes a conductive pad to be brought into contact with a conductor of the detachable electronic device.

Example 128 may include at least a portion of the subject matter of example 127, where the first connector includes means to physically secure the detachable electronic device to the first connector.

Example 129 may include at least a portion of the subject matter of example 127, where the detachable electronic device includes means to physically secure the detachable electronic device to the first connector.

Example 130 may include at least a portion of the subject matter of example 129, where the means include a conductive clip, and the conductive clip includes the conductor of the detachable electronic device.

Example 131 may include at least a portion of the subject matter of any one of examples 124-130, where the first connector includes a recess on at least one side of the first connector to accept a layer of substrate to be in contact with the first connector on the at least one side.

Example 132 may include at least a portion of the subject matter of example 131, where the recess includes a recess around a perimeter of the first connector to accept the layer of the substrate when the first connector is passed through an opening in the substrate.

Example 133 may include at least a portion of the subject matter of any one of examples 131-132, where the substrate includes fabric.

Example 134 may include at least a portion of the subject matter of example 134, where the fabric includes one of upholstery fabric or fabric of a wearable device.

Example 135 is an apparatus including: one or more liquid metal wires, including a channel to house liquid metal; and a connector including a housing, where the housing is to interface with the channel of the liquid metal wire and allow the liquid metal to pass from the channel into the housing to bring the liquid metal into contact with one or more conductive pads within the housing.

Example 136 may include at least a portion of the subject matter of example 135, where the connector connects in-line with the one or more liquid metal wires.

Example 137 may include at least a portion of the subject matter of any one of examples 135-136 where the housing includes cavities aligned with the conductive pads to direct the liquid metal to the one or more conductive pads.

Example 138 may include at least a portion of the subject matter of example 137, where the one or more liquid metal wires include a plurality of liquid metal wires, the one or more conductive pads include a plurality of conductive pads, and the housing is separately direct liquid metal from each of the plurality of liquid metal wires to a respective one of the plurality of conductive pads.

Example 139 may include at least a portion of the subject matter of any one of examples 135-138, where the liquid metal includes a gallium-based metal.

Example 140 may include at least a portion of the subject matter of example 139, where the liquid metal includes eutectic gallium indium (EGaIn).

Example 141 may include at least a portion of the subject matter of any one of examples 135-140, further including a touch sensor including: the one or more liquid metal wires; a microprocessor; detection logic including hardware circuitry to: detect a change in an electrical attribute of the one or more liquid metal wires based on a depression of the one or more liquid metal wires; and indicate a touch event corresponding to the depression of the one or more liquid metal wires based on the change in the electrical attribute.

Example 142 may include at least a portion of the subject matter of any one of examples 135-141, where the one or more liquid metal wires are included in a garment.

Example 143 may include at least a portion of the subject matter of example 142, where the liquid metal wires are interwoven in the garment.

Example 144 may include at least a portion of the subject matter of any one of examples 135-143, where the housing is sealed to each of the channels to prevent leakage of the liquid metal.

Example 145 is an electrical cable including: an elastomeric sheath including a plurality of cavities to define a plurality of respective channels, where each of the plurality of cavities is adapted to enclose and contain liquid metal to form a respective one of a plurality of wires to be included in the cable.

Example 146 may include at least a portion of the subject matter of example 145, where the plurality of wires embody the one or more wires of the apparatus of any one of examples 135-144.

Example 147 is an article including any one of examples 1-27, 32-59, and 63-146.

Example 148 may include at least a portion of the subject matter of example 147, where the article includes a garment.

Example 149 may include at least a portion of the subject matter of f example 148, where the garment includes an elastomeric athletic garment.

Example 150 may include at least a portion of the subject matter of example 147, where the article includes footwear.

Example 151 may include at least a portion of the subject matter of example 147, where the article includes upholstery.

Example 152 may include at least a portion of the subject matter of example 147, where the article includes wallpaper.

Example 153 may include at least a portion of the subject matter of example 147, where the article includes athletic equipment.

Example 154 may include at least a portion of the subject matter of example 147, where the article includes a medical device.

Example 155 may include at least a portion of the subject matter of example 147, where the article includes a headphone cord.

Example 156 may include at least a portion of the subject matter of example 147, where the article includes a connector assembly.

Example 157 may include at least a portion of the subject matter of example 156, where the article includes a USB connector assembly.

Thus, particular embodiments of the subject matter have been described. Other embodiments are within the scope of the following claims. In some cases, the actions recited in the claims can be performed in a different order and still achieve desirable results. In addition, the processes depicted in the accompanying figures do not necessarily require the particular order shown, or sequential order, to achieve desirable results.

A detailed description has been given with reference to specific exemplary embodiments. It will, however, be evident that various modifications and changes may be made thereto without departing from the broader spirit and scope of the invention as set forth in the appended claims. The specification and drawings are, accordingly, to be regarded in an illustrative sense rather than a restrictive sense. Furthermore, the foregoing use of embodiment and other exemplarily language does not necessarily refer to the same embodiment or the same example, but may refer to different and distinct embodiments, as well as potentially the same embodiment.

The invention claimed is:

1. An apparatus comprising:
a connector comprising:
an opening to couple to a channel; and
a reservoir comprising a solid metal conductor, wherein the reservoir is to receive liquid metal to substantially fill a volume of the reservoir and extend through the opening into the channel, wherein the channel, when filled with the liquid metal, forms at least a portion of a liquid metal circuit.

2. The apparatus of claim 1, wherein the opening comprises a conduit and the conduit protrudes from an exterior surface of the connector.

3. The apparatus of claim 2, wherein the conduit is to be inserted into an opening of the channel to connect to the channel.

4. The apparatus of claim 2, wherein an element of the channel is to be inserted into an opening of the conduit to connect the conduit to the channel.

5. The apparatus of claim 2, wherein cross-sectional geometry of the channel corresponds to cross-sectional geometry of the conduit.

6. The apparatus of claim 1, wherein the conductor comprises at least a portion of the surface of the reservoir.

7. The apparatus of claim 1, wherein the conduit is sealed to the tubular channel to form a continuous volume formed by the channel and reservoir.

8. The apparatus of claim 1, wherein the connector further comprising another opening to accept injection of the liquid metal into the reservoir.

9. The apparatus of claim 8, wherein the other opening comprises a cap made of self-healing material.

10. The apparatus of claim 1, further comprising an electronic device coupled to the connector, wherein the conductor is to provide an electrical connection from the liquid metal to the electronic device.

11. The apparatus of claim 10, wherein the electronic device comprises the connector and the connector is adapted to connect to another device.

12. The apparatus of claim 10, wherein the electronic device comprises one of a processor, sensor, actuator, memory element, antennae, or user interface device.

13. The apparatus of claim 1, wherein the connector further comprises:
a plurality of conduits comprising the conduit; and
a plurality of reservoirs comprising the reservoir, wherein each of the plurality of conduits is to connect a respective liquid metal wire to a respective one of the plurality of reservoirs, and each of the plurality of reservoirs comprises a respective conductor.

14. A method comprising:
coupling one or more conduits of a connector to a channel, wherein the connector comprises one or more reservoirs corresponding to the one or more conduits, each of the one or more reservoirs comprises a respective solid metal conductor, and the one or more reservoirs when filled with liquid metal bring the liquid metal into contact with the conductor of the reservoir; and
injecting liquid metal to fill the one or more reservoirs and enter the channel via the one or more conduits.

15. The method of claim 14, further comprising fixing an opening of the channel to the connector.

16. The method of claim 14, wherein the opening comprises a first opening, the channel comprises the first opening at a first end of the cable and a second opening at a second end of the cable, the connector comprises a first connector, and the conduit of the first connector is connected to the channel using the first opening, and the method further comprises:

inserting a conduit of a second connector into the second opening of the channel to connect the second connector to the channel, wherein the second connector comprises a reservoir and connecting the second connector to the channel forms a continuous volume of liquid metal comprising the channel, the reservoir of the first connector, and the reservoir of the second connector.

17. The method of claim 14, wherein the liquid metal comprises eutectic gallium indium (EGaIn).

18. An apparatus comprising:
    a first electronic component coupled to a first connector;
    a second electronic component coupled to a second connector; and
    a liquid metal wire connecting the first connector to the second connector,
    wherein the first connector comprises:
        a hollow conduit configured to connect to channel, wherein the liquid metal wire comprises the channel; and
        a reservoir comprising a solid metal conductor, wherein the reservoir is to be substantially filled with liquid metal extending into the liquid metal wire to bring the liquid metal into contact with the solid metal conductor, and the solid metal conductor is conductively connected to circuitry of the first electronic component.

19. The apparatus of claim 18, wherein the liquid metal wire is fastened to fabric.

20. The apparatus of claim 18, wherein the apparatus comprises a wearable device.

* * * * *